United States Patent
Yang et al.

(10) Patent No.: US 12,144,609 B2
(45) Date of Patent: Nov. 19, 2024

(54) METHOD AND APPARATUS FOR SETTING SPORTS MODE

(71) Applicant: HUAWEI TECHNOLOGIES CO., LTD., Guangdong (CN)

(72) Inventors: Bin Yang, Beijing (CN); Yu Wang, Beijing (CN); Xiaohan Chen, Shenzhen (CN)

(73) Assignee: HUAWEI TECHNOLOGIES CO., LTD., Guangdong (CN)

( * ) Notice: Subject to any disclaimer, the term of this patent is extended or adjusted under 35 U.S.C. 154(b) by 1030 days.

(21) Appl. No.: 17/058,909

(22) PCT Filed: May 28, 2019

(86) PCT No.: PCT/CN2019/088691
§ 371 (c)(1),
(2) Date: Nov. 25, 2020

(87) PCT Pub. No.: WO2019/228315
PCT Pub. Date: Dec. 5, 2019

(65) Prior Publication Data
US 2021/0197024 A1     Jul. 1, 2021

(30) Foreign Application Priority Data
May 31, 2018    (CN) .......................... 201810552311.7

(51) Int. Cl.
*A61B 5/11*     (2006.01)
*A63B 71/06*     (2006.01)
*G04G 9/00*     (2006.01)

(52) U.S. Cl.
CPC ......... *A61B 5/1123* (2013.01); *A63B 71/0686* (2013.01); *A63B 2220/40* (2013.01);
(Continued)

(58) Field of Classification Search
CPC .............. A61B 5/1123; A63B 71/0686; A63B 2220/40; A63B 2220/836; A63B 2244/20; G04G 9/0064
See application file for complete search history.

(56) References Cited

U.S. PATENT DOCUMENTS 10,223,557 B2 *   3/2019   Malcolm ............ A63B 21/4039
10,405,797 B1 *   9/2019   Uehara ................ A61B 5/1107
(Continued)

FOREIGN PATENT DOCUMENTS

CN     103631132 A    3/2014
CN     104134318 A    11/2014
(Continued)

*Primary Examiner* — Elias Desta
(74) *Attorney, Agent, or Firm* — WOMBLE BOND DICKINSON (US) LLP

(57) ABSTRACT

A method and an apparatus for setting a sports mode are provided. Two metal endpoints on an outer surface of an intelligent device are respectively used as an output end and a receive end of signals. A signal sent by the output end is compared with a signal received by the receive end to determine whether the intelligent device currently meets a preset condition. First sports characteristic data detected by a sports sensing apparatus is obtained to determine whether the first sports characteristic data matches preset sports characteristic data corresponding to a swimming mode. When two determining results are both "yes", it can be determined that the intelligent device meets a setting condition of the swimming mode.

20 Claims, 9 Drawing Sheets

(52) U.S. Cl.
CPC ..... *A63B 2220/836* (2013.01); *A63B 2244/20* (2013.01); *G04G 9/0064* (2013.01)

(56) References Cited

U.S. PATENT DOCUMENTS

| | | |
|---|---|---|
| 2012/0118084 A1 | 5/2012 | Klose et al. |
| 2015/0320575 A1* | 11/2015 | Joshi .................. A61F 2/54 623/25 |
| 2016/0344230 A1 | 11/2016 | Chan |

FOREIGN PATENT DOCUMENTS

| | | | |
|---|---|---|---|
| CN | 105068656 | A | 11/2015 |
| CN | 105244964 | A | 1/2016 |
| CN | 104161524 | B | 4/2016 |
| CN | 106175781 | A | 12/2016 |
| CN | 106296427 | A | 1/2017 |
| CN | 106730651 | A | 5/2017 |
| CN | 106873716 | A | 6/2017 |
| GB | 2509945 | A | 7/2014 |
| WO | 2010113135 | A1 | 10/2010 |

\* cited by examiner

METHOD AND APPARATUS FOR SETTING SPORTS MODE

This application is a National Stage of International Application No. PCT/CN2019/088691, filed on May 28, 2019, which claims priority to Chinese Patent Application No. 201810552311.7, filed on May 31, 2018. Both of the aforementioned applications are incorporated by reference herein in its entirety.

TECHNICAL FIELD

This application relates to the field of intelligent control technologies, and in particular, to a method and an apparatus for setting a sports mode.

BACKGROUND

An intelligent device such as a sports bracelet can record and process various types of sports data of a user, to reflect a sports status of the user. For example, when identifying that the user is swimming, the intelligent device may set a sports mode to a swimming mode, so that the intelligent device can record swimming-related sports data for the user in the swimming mode. However, currently, a conventional intelligent device usually cannot accurately identify whether the user is swimming, and therefore identification performed by the intelligent device on the swimming mode is usually incorrect. Consequently, the intelligent device cannot accurately record and process the swimming-related sports data for the user.

SUMMARY

A technical problem to be resolved in embodiments of this application is to provide a method and an apparatus for setting a sports mode, so that an intelligent device can more accurately identify whether a user is swimming, to more accurately record and process swimming-related sports data for the user.

According to a first aspect, an embodiment of this application provides a method for setting a sports mode. An intelligent device outputs a first electrical signal of a preset frequency by using an output end and receives a second electrical signal by using a receive end, where the output end and the receive end are two metal endpoints on an outer surface of the intelligent device; the intelligent device obtains first sports characteristic data detected by a sports sensing apparatus, where the sports sensing apparatus is mounted in the intelligent device; and the intelligent device sets a sports status mode to a swimming state mode if a setting condition of the swimming state mode is met, where the setting condition includes: a change situation between the second electrical signal and the first electrical signal meets a preset condition, a frequency of the second electrical signal matches the preset frequency, and the first sports characteristic data matches preset sports characteristic data corresponding to the swimming state mode. It may be learned that in this embodiment of this application, the two metal endpoints on the outer surface of the intelligent device are respectively used as the output end and the receive end of signals. A signal sent by the output end is compared with a signal received by the receive end to determine whether the intelligent device currently meets the preset condition, so that it can be determined that the intelligent device meets the setting condition of the swimming mode, or in other words, the intelligent device is enabled to accurately identify the swimming mode. Therefore, the intelligent device can accurately record and process swimming-related sports data for a user.

In an embodiment, the preset condition is: the frequency of the second electrical signal matches a frequency of the first electrical signal. In an example, the first electrical signal and the second electrical signal are square wave signals. In this way, in an embodiment of this application, a signal sent by the output end is compared with a signal received by the receive end to determine whether the intelligent device is currently in a liquid environment. When a frequency of the signal sent by the output end matches a frequency of the signal received by the receive end, it may be determined that the intelligent device is currently in the liquid environment. This can avoid a problem that the intelligent device makes a misjudgment on the swimming mode due to interference from factors such as static electricity, so that it can be accurately detected whether the intelligent device is in the liquid environment, and the intelligent device is enabled to accurately identify the swimming mode. Therefore, the intelligent device can accurately record and process swimming-related sports data for a user.

In an embodiment, the method further includes: the intelligent device outputs a third electrical signal by using the output end and receives a fourth electrical signal by using the receive end; and the intelligent device calculates an impedance value between the output end and the receive end based on the third electrical signal and the fourth electrical signal, where correspondingly, the setting condition further includes: the impedance value is within a preset impedance range of water quality corresponding to a swimming state. In an example, the third electrical signal and the fourth electrical signal are direct-current signals. In this way, in an embodiment of this application, the intelligent device can automatically enter the swimming mode only when it is determined that the intelligent device is in a liquid environment and the liquid environment is a swimming environment. This avoids a problem that the intelligent device incorrectly switches to the swimming mode when the intelligent device is in a non-swimming liquid environment. In addition, a problem that the intelligent device makes a misjudgment on the swimming mode due to interference from factors such as static electricity is overcome, and the intelligent device is enabled to more accurately identify the swimming mode. Therefore, the intelligent device can accurately enter the swimming mode, and record and process swimming-related sports data for a user.

In an embodiment, the preset condition is: an impedance value between the output end and the receive end that is calculated based on the first electrical signal and the second electrical signal is within a preset impedance range. In this way, in this embodiment of this application, an impedance value of an environment in which the intelligent device is currently located may be calculated by obtaining a signal sent by the output end and a signal received by the receive end. When the impedance value obtained through calculation is within a preset impedance range corresponding to a swimming environment, it may be determined that the intelligent device is in the swimming environment, so that the intelligent device automatically enters the swimming mode. This avoids a problem that the intelligent device incorrectly switches to the swimming mode when the intelligent device is in a non-swimming liquid environment, and enables the intelligent device to more accurately identify the swimming mode. Therefore, the intelligent device can accurately record and process swimming-related sports data for a user.

In an embodiment, the sports sensing apparatus in the foregoing implementation may include an acceleration sensor and/or a gyroscope apparatus. The acceleration sensor is configured to detect sports characteristic data indicating an acceleration change, and the gyroscope apparatus is configured to detect sports characteristic data indicating an angle change.

In an embodiment, the method for setting a sports mode not only can accurately set the swimming mode, but also can accurately exit the swimming mode. A specific implementation includes but is not limited to: the intelligent device outputs a fifth electrical signal of the preset frequency by using the output end and receives a sixth electrical signal by using the receive end; and the intelligent device sets a sports mode status to a non-swimming mode state if a frequency of the sixth electrical signal does not match the preset frequency of the fifth electrical signal; or the intelligent device obtains second sports characteristic data detected by the sports sensing apparatus; and the intelligent device sets a sports mode status to a non-swimming mode state if the second sports characteristic data does not match the preset sports characteristic data. In this way, in an embodiment of this application, when the sports mode is the swimming mode, whether a user exits a swimming sport may be further identified, to accurately exit the swimming mode, so that the intelligent device can automatically and accurately switch from the swimming mode to a non-swimming mode, thereby improving intelligence of the intelligent device and optimizing user experience.

According to a second aspect, an embodiment of this application further provides an intelligent device for setting a sports mode, including: a first transceiver module, configured to output a first electrical signal by using an output end and receive a second electrical signal by using a receive end, where the output end and the receive end are two metal endpoints on an outer surface of the intelligent device; a first obtaining module, configured to obtain first sports characteristic data detected by a sports sensing apparatus, where the sports sensing apparatus is mounted in the intelligent device; and a first setting module, configured to set a sports mode to a swimming mode if a setting condition of the swimming mode is met, where the setting condition includes: a change situation between the second electrical signal and the first electrical signal meets a preset condition, and the first sports characteristic data matches preset sports characteristic data corresponding to the swimming mode.

In an embodiment, the preset condition is: a frequency of the second electrical signal matches a frequency of the first electrical signal. In an example, the first electrical signal and the second electrical signal are square wave signals.

In an embodiment, the intelligent device further includes: a second transceiver module, configured to output a third electrical signal by using the output end and receive a fourth electrical signal by using the receive end; and a calculation module, configured to calculate an impedance value between the output end and the receive end based on the third electrical signal and the fourth electrical signal, where correspondingly, the setting condition further includes: the impedance value is within a preset impedance range. In an example, the third electrical signal and the fourth electrical signal are direct-current signals.

In an embodiment, the preset condition is: an impedance value between the output end and the receive end that is calculated based on the first electrical signal and the second electrical signal is within a preset impedance range.

In an embodiment, the sports sensing apparatus in the foregoing implementation may include an acceleration sensor and/or a gyroscope apparatus. The acceleration sensor is configured to detect sports characteristic data indicating an acceleration change, and the gyroscope apparatus is configured to detect sports characteristic data indicating an angle change.

In an embodiment, the intelligent device for setting a sports mode not only can accurately set the swimming mode, but also can accurately exit the swimming mode. A specific implementation includes but is not limited to: a third transceiver module, configured to output a fifth electrical signal by using the output end and receive a sixth electrical signal by using the receive end; and a second setting module, configured to set the sports mode to a non-swimming mode if a frequency of the sixth electrical signal does not match a frequency of the fifth electrical signal; or a second obtaining module, configured to obtain second sports characteristic data detected by the sports sensing apparatus; and a third setting module, configured to set the sports mode to a non-swimming mode if the second sports characteristic data does not match the preset sports characteristic data.

The intelligent device for setting a sports mode provided in the second aspect corresponds to the method for setting a sports mode provided in the first aspect. Therefore, for the possible implementations of the intelligent device for setting a sports mode provided in the second aspect, refer to the possible implementations of the method for setting a sports mode provided in the first aspect.

According to a third aspect, an embodiment of this application further provides an intelligent device for setting a sports mode, and the intelligent device includes an output end, a receive end, a sports sensing apparatus, and a processor.

The processor is configured to: read a software instruction in a memory, and execute the software instruction to implement the following operations: The output end is driven to output a first electrical signal and the receive end is driven to receive a second electrical signal, where the output end and the receive end are two metal endpoints on an outer surface of the intelligent device; the sports sensing apparatus is driven to detect first sports characteristic data, where the sports sensing apparatus is mounted in the intelligent device; and a sports mode is set to a swimming mode if a setting condition of the swimming mode is met, where the setting condition includes: a change situation between the second electrical signal and the first electrical signal meets a preset condition, and the first sports characteristic data matches preset sports characteristic data corresponding to the swimming mode.

In an embodiment, the preset condition is: a frequency of the second electrical signal matches a frequency of the first electrical signal. In an example, the first electrical signal and the second electrical signal are square wave signals.

In an embodiment, the processor is configured to: read the software instruction in the memory, and further execute the software instruction to implement the following operations: The output end is driven to output a third electrical signal and the receive end is driven to receive a fourth electrical signal; and an impedance value between the output end and the receive end is calculated based on the third electrical signal and the fourth electrical signal, where correspondingly, the setting condition further includes: the impedance value is within a preset impedance range. In an example, the third electrical signal and the fourth electrical signal are direct-current signals.

In an embodiment, the preset condition is: an impedance value between the output end and the receive end that is calculated based on the first electrical signal and the second electrical signal is within a preset impedance range.

In an embodiment, the sports sensing apparatus in the foregoing implementation may include an acceleration sensor and/or a gyroscope apparatus. The acceleration sensor is configured to detect sports characteristic data indicating an acceleration change, and the gyroscope apparatus is configured to detect sports characteristic data indicating an angle change.

In an embodiment, the intelligent device for setting a sports mode not only can accurately set the swimming mode, but also can accurately exit the swimming mode. A specific implementation includes but is not limited to: after the intelligent device sets the sports mode to the swimming mode, the processor is configured to: read the software instruction in the memory, and further execute the software instruction to implement the following operations: The output end is driven to output a fifth electrical signal and the receive end is driven to receive a sixth electrical signal; and the sports mode is set to a non-swimming mode if a frequency of the sixth electrical signal does not match a frequency of the fifth electrical signal; or after the intelligent device sets the sports mode to the swimming mode, the processor is configured to: read the software instruction in the memory, and further execute the software instruction to implement the following operations: The sports sensing apparatus is driven to detect second sports characteristic data; and the sports mode is set to a non-swimming mode if the second sports characteristic data does not match the preset sports characteristic data.

It may be understood that the intelligent device is a wearable device.

The intelligent device for setting a sports mode provided in the third aspect corresponds to the method for setting a sports mode provided in the first aspect. Therefore, for the possible implementations of the intelligent device for setting a sports mode provided in the third aspect, refer to the possible implementations of the method for setting a sports mode provided in the first aspect.

According to a fourth aspect, an embodiment of this application provides a computer-readable storage medium including an instruction. When the instruction is run on a computer, the computer is enabled to perform the method in any one of the first aspect and the possible designs of the first aspect.

According to a fifth aspect, an embodiment of this application provides a computer program product including an instruction. When the computer program product runs on a computer, the computer is enabled to perform the method in any one of the first aspect and the possible designs of the first aspect.

DESCRIPTION OF EMBODIMENTS

Figure 1:
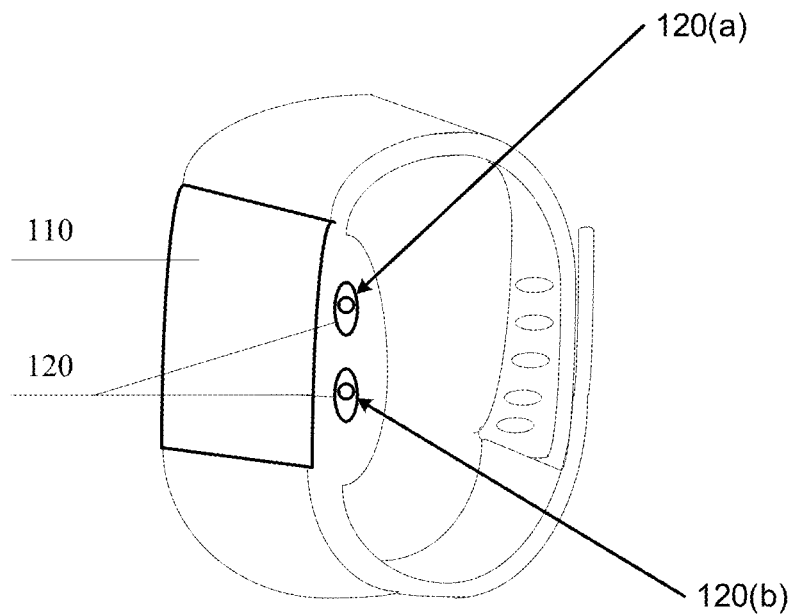
FIG. 1 is a schematic structural diagram of an intelligent device according to an embodiment of this application.

Currently, an intelligent device (for example, a wearable device such as a sports bracelet or a smartwatch) is configured to record various types of sports data of a user wearing the intelligent device, to reflect a sports mode of the user. With continuous development of technologies, to meet a requirement of the user, the sports mode of the intelligent device may include a swimming mode in addition to a running mode, a cycling mode, and the like. The swimming mode is used to record sports data of the user when the user swims in water, including parameters such as a swimming distance, a time, and a speed, to intelligently feed an actual sports status of the user back to the user.

However, in the prior art, to record swimming data in the swimming mode, the user usually needs to perform corresponding manual setting on the intelligent device or a mobile terminal connected to the intelligent device before swimming, to switch the sports mode of the intelligent device to the swimming mode. After swimming, the user also needs to perform manual setting to enable the intelligent device to exit the swimming mode. It may be learned that a manner used by the intelligent device to set the sports mode is basically manual setting, and the user needs to perform tedious manual operations. Consequently, user experience is relatively poor.

To improve user experience, currently, some intelligent devices may automatically enter and exit the swimming mode.

The inventor finds through research that a method for determining, by the existing intelligent device, that the user is in the swimming mode is specifically: detecting whether a short-circuit phenomenon occurs at two metal test points on an outer surface of the intelligent device, to determine whether the user is in a liquid environment. Although the automatic setting of the swimming mode improves application experience of the user on the intelligent device, the determining whether the intelligent device is in the liquid environment by merely relying on the short-circuit phenomenon occurred on the metal test points is very easily affected by static electricity around the intelligent device, or is interfered with by factors such as contact between the intelligent device and a non-swimming environment such as purified water or tap water. Consequently, setting by the intelligent device for the swimming mode is inaccurate, and even an error is caused, thereby easily causing the intelligent device to make a misjudgment on the swimming mode.

Based on this, to overcome interference from factors such as static electricity around an intelligent device and improve accuracy of setting a sports mode to a swimming mode by the intelligent device, an embodiment of this application provides a method for setting a sports mode. The intelligent device may consider two aspects: an environment in which the intelligent device is located and sports characteristic data generated by the intelligent device. In a first aspect, electrical signals are received and sent between an output end and a receive end of the intelligent device, and the received and sent electrical signals are compared to accurately determine whether the intelligent device is in a liquid environment, thereby avoiding electrostatic interference. Specifically, even if static electricity appears around the intelligent device, the receive end is instantly temporarily connected to the output end. In this case, although the receive end may receive an electrical signal output by the output end, the electrical signal does not continuously appear, and does not match an electrical signal output by the output end. In another aspect, a sports sensing apparatus on the intelligent device detects sports characteristic data, and determines whether the sports characteristic data obtained through detection conforms to preset sports characteristic data corresponding to the swimming mode. It may be learned that the method for setting a sports mode can enable the intelligent device to accurately identify the swimming mode, so that the intelligent device can accurately record and process swimming-related sports data for a user.

Generally, a swimming pool requires disinfection, chlorine removal, and the like. Therefore, water quality in the swimming pool is within a specific impedance range. In the foregoing first aspect, an impedance value between the output end and the receive end of the intelligent device may be calculated by comparing the electrical signals received and sent between the output end and the receive end of the intelligent device, and it may be accurately determined whether the impedance value is within a preset impedance range of water quality corresponding to the swimming mode, that is, it is accurately determined whether an environment in which the intelligent device is currently located is an environment in which water quality is suitable for swimming, so that a misjudgment caused by contact between the intelligent device and a non-swimming environment such as purified water or tap water is ruled out. Specifically, when the intelligent device is in contact with the purified water, the calculated impedance value is an impedance value of the purified water, and it is impossible to determine that the user is in the environment in which the water quality is suitable for swimming.

With reference to the accompanying drawings, the following describes in detail, by using embodiments, specific implementations of the method for setting a sports mode provided in this embodiment of this application.

FIG. 1 is a schematic structural diagram of an intelligent device. Referring to FIG. 1, the intelligent device is a smart band, and the smart band includes a display apparatus 110 and two metal endpoints 120 (e.g., 120(*a*), 120(*b*)). The two metal endpoints 120 (e.g., 120(*a*), 120(*b*)) may be configured to charge the smart band. The method for setting a sports mode provided in this application may be applied to, but is not limited to, the intelligent device shown in FIG. 1. For example, optionally, the intelligent device does not include the display apparatus 110. One of the two metal endpoints 120 (e.g., 120(*a*), 120(*b*)) is configured to output a first electrical signal (e.g., 120(*a*) or 120(*b*)), and the other metal endpoint (e.g., 120(*b*) or 120(*a*)) is configured to receive a second electrical signal. That the two metal endpoints 120 (e.g., 120(*a*), 120(*b*)) are on an outer surface of the smart band means that the metal endpoints 120 may be in contact with an external water environment when a user wears the smart band, and the two metal endpoints 120 (e.g., 120(*a*), 120(*b*)) may be on a side surface of the display apparatus 110 shown in FIG. 1, or may be on a front surface of a wrist strap of the band, a back surface of the wrist strap, or another location. The front surface of the wrist strap is a surface that is of the wrist strap of the band and that is not in contact with skin of the user, and the back surface of the wrist strap is a surface that is of the wrist strap of the band and that is in contact with the skin of the user. A location of the metal endpoint 120 (e.g., 120(*a*), 120(*b*)) is not specifically limited in this application. The smart band further includes a sports sensing apparatus mounted in the band, and the sports sensing apparatus is configured to detect sports characteristic data.

The following uses the smart band shown in FIG. 1 as an example for description. For a manner of setting a sports mode by another device, refer to the related descriptions of the smart band.

Figure 2:
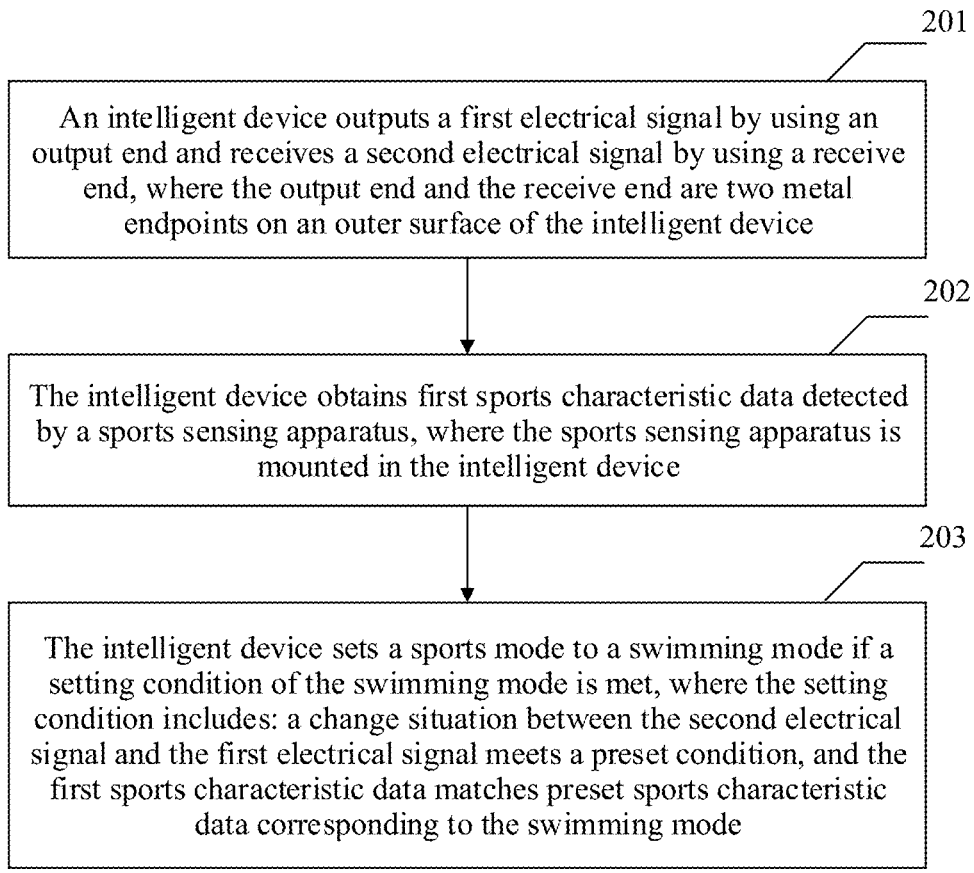
FIG. 2 is a schematic flowchart of a method for setting a sports mode according to an embodiment of this application.

FIG. 2 is a schematic flowchart of a method for setting a sports mode according to an embodiment of this application. Referring to FIG. 2, in an embodiment, an intelligent device may receive and send electrical signals between a receive end and an output end of the intelligent device to accurately determine whether the intelligent device is in a swimming environment, and accurately determine whether sports characteristic data generated by the intelligent device conforms to sports characteristic data of a swimming state. In other words, the intelligent device accurately identifies a swimming mode by considering two aspects: accurately determining an environment in which the intelligent device is located and the generated sports characteristic data.

The method for setting a sports mode provided in this embodiment may include the following operations.

Operation 201: An intelligent device outputs a first electrical signal by using an output end and receives a second electrical signal by using a receive end, where the output end and the receive end are two metal endpoints on an outer surface of the intelligent device.

Referring to FIG. 1, two metal endpoints 120 are disposed on the outer surface of the intelligent device. One of the two metal endpoints 120 is used as the output end, and the other endpoint is used as the receive end. After the output end outputs the first electrical signal, the receive end receives the second electrical signal. In one case, the two metal endpoints 120 may be two metal endpoints on a charging interface of the intelligent device. In another case, the two metal endpoints may be independently disposed for setting a sports mode and are different from other two metal endpoints on the charging interface.

Operation 202: The intelligent device obtains first sports characteristic data detected by a sports sensing apparatus, where the sports sensing apparatus is mounted in the intelligent device.

It may be understood that the sports sensing apparatus is integrated into the intelligent device. In this case, the first sports characteristic data detected by the sports sensing apparatus may indicate sports characteristic data of the intelligent device, to represent a sports mode of a user wearing the intelligent device.

In an embodiment, the sports sensing apparatus may include an acceleration sensor and/or a gyroscope apparatus. The acceleration sensor is configured to detect sports characteristic data indicating an acceleration change, and the gyroscope apparatus is configured to detect sports characteristic data indicating an angle change. In this case, the first sports characteristic data may include the sports characteristic data that is detected by the acceleration sensor and that indicates the acceleration change, and/or the sports characteristic data that is detected by the gyroscope apparatus and that indicates the angle change.

It may be learned that in this embodiment, the first sports characteristic data of the intelligent device is detected by using the sports sensing apparatus in the intelligent device, so that the sports characteristic data of the intelligent device can be relatively comprehensively and accurately obtained, thereby providing a good data basis for subsequently setting a sports mode.

It should be noted that there is no limitation on a sequence of performing operations 201 and 202. Operation 201 may be performed before operation 202, or operation 202 may be performed before operation 201, or operations 201 and 202 may be performed at the same time. This is not specifically limited herein.

Operation 203: The intelligent device sets a sports mode to a swimming mode if a setting condition of the swimming mode is met, where the setting condition includes: a change situation between the second electrical signal and the first electrical signal meets a preset condition, and the first sports characteristic data matches preset sports characteristic data corresponding to the swimming mode.

A plurality of sports modes are usually configured on the intelligent device. For example, the sports modes may include a running mode, a swimming mode, a cycling mode, and a step counting mode. The intelligent device may set a current sports mode of a user based on a sports status of the user, and records sports data of the user in the sports mode. Setting a sports mode to a swimming mode means that when it is detected that the current sports mode of the user is the swimming mode, the intelligent device switches from a current non-swimming sports mode to the swimming mode, to accurately record swimming data for the user. For example, when the user participates in a triathlon, before the user swims, the sports mode of the intelligent device is the step counting mode. After the user enters water and starts swimming, the intelligent device switches the sports mode from the step counting mode to the swimming mode.

It may be understood that, to set the sports mode of the intelligent device to the swimming mode, two conditions need to be met: Condition 1: The change situation between the second electrical signal and the first electrical signal meets the preset condition. Condition 2: The first sports characteristic data matches the preset sports characteristic data corresponding to the swimming mode.

The condition 1 may include: a frequency of the second electrical signal matches a frequency of the first electrical signal, and/or an impedance value between the output end and the receive end that is calculated based on the first electrical signal and the second electrical signal is within a preset impedance range. For details, respectively refer to the descriptions in the embodiments shown in FIG. 3 and FIG. 4.

For the condition 2, after the intelligent device detects the first sports characteristic data by using the sports sensing apparatus, the intelligent device may analyze the first sports characteristic data, and determine whether the first sports characteristic data matches the preset sports characteristic data corresponding to the prestored swimming mode. When the first sports characteristic data matches the preset sports characteristic data corresponding to the swimming mode, it indicates that a sports characteristic of the user wearing the intelligent device is consistent with a sports characteristic corresponding to swimming. The preset sports characteristic data corresponding to the swimming mode may include sports characteristic data that is separately set based on different swimming postures, for example, a hand movement amplitude and a quantity of hand movement times during breaststroke. The intelligent device may further determine, based on the first sports characteristic data, that a swimming posture of the user is freestyle, breaststroke, butterfly, backstroke, medley, or the like.

It may be learned that in an embodiment, when a change situation between a signal sent by the output end and a signal received by the receive end meets the preset condition, it may be determined that the intelligent device is currently in a swimming environment, so that it can be accurately detected that the intelligent device is in the swimming environment, and the intelligent device is enabled to accurately identify the swimming mode. Therefore, the intelligent device can accurately record and process swimming-related sports data for the user. The swimming-related sports data may include information such as a swimming posture, a total time, a segmentation time, a distance, an average speed, a segmentation speed, a quantity of hand movement times of each swimming posture, and consumed calories.

Figure 3:
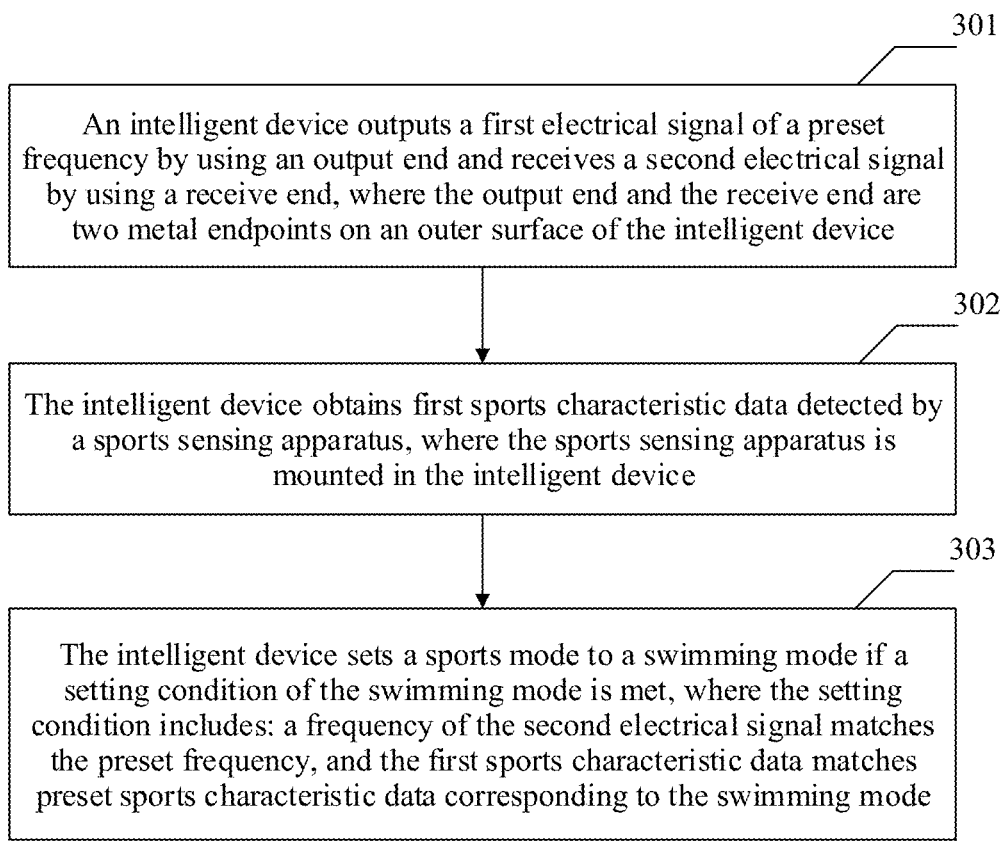
FIG. 3 is a schematic flowchart of a method for setting a sports mode according to an embodiment of this application.

FIG. 3 is a schematic flowchart of a method for setting a sports mode according to an embodiment of this application. Referring to FIG. 3, in an embodiment, an intelligent device may receive and send electrical signals of a preset frequency between a receive end and an output end of the intelligent device to accurately determine whether the intelligent device is in a liquid environment, and accurately determine whether sports characteristic data generated by the intelligent device conforms to sports characteristic data of swimming. In other words, the intelligent device accurately identifies a swimming mode by considering two aspects: accurately determining an environment in which the intelligent device is located and the generated sports characteristic data.

The method for setting a sports mode provided in this embodiment may include the following operations.

Operation 301: An intelligent device outputs a first electrical signal of a preset frequency by using an output end and receives a second electrical signal by using a receive end, where the output end and the receive end are two metal endpoints on an outer surface of the intelligent device.

It may be understood that, if the intelligent device is in a liquid, that is, both the output end and the receive end are located in the liquid, due to electrical conductivity of the liquid, a frequency of the second electrical signal received by using the receive end needs to match a frequency of the first electrical signal output by the output end.

To simply generate and output the first electrical signal, the output end may select a square wave signal that consumes fewer resources as the first electrical signal, that is, the first electrical signal output by the output end may be a square wave signal of the preset frequency (for example, 10 kHz). If the output end is connected to the receive end, that is, if the frequency of the second electrical signal matches the frequency of the first electrical signal, the second electrical signal may also be a square wave signal.

It may be understood that, to improve stability of an electrical signal, the output end of the intelligent device may continuously output the first electrical signal of the preset frequency for one minute. For example, the output end continuously outputs a square wave signal of 10 kHz for one minute. In this case, provided that the output end is connected to the receive end, the receive end may receive the second electrical signal, for example, continuously receive a square wave signal of 10 kHz for one minute.

Operation 302: The intelligent device obtains first sports characteristic data detected by a sports sensing apparatus, where the sports sensing apparatus is mounted in the intelligent device.

It should be noted that, for descriptions of operation 302, refer to the descriptions of operation 202. In addition, there is no limitation on a sequence of performing operations 301 and 302. Operation 301 may be performed before operation 302, or operation 302 may be performed before operation 301, or operations 301 and 302 may be performed at the same time. This is not specifically limited herein.

Operation 303: The intelligent device sets a sports mode to a swimming mode if a setting condition of the swimming mode is met, where the setting condition includes: a frequency of the second electrical signal matches the preset frequency, and the first sports characteristic data matches preset sports characteristic data corresponding to the swimming mode.

It may be determined, based on the second electrical signal received by the receive end of the intelligent device in operation 301 and the first sports characteristic data detected by the sports sensing apparatus of the intelligent device in operation 302, whether the intelligent device currently meets the preset setting condition of the swimming mode. The setting condition of the swimming mode includes but is not limited to the following: Condition 1: The frequency of the second electrical signal matches the preset frequency. Condition 2: The first sports characteristic data matches the preset sports characteristic data corresponding to the swimming mode. When both the condition 1 and the condition 2 are met, it indicates that the intelligent device is currently in the swimming mode. In this case, the intelligent device sets the sports mode to the swimming mode, so that the intelligent device can accurately record and process swimming-related sports data for a user.

For the condition 1, after the intelligent device outputs the first electrical signal of the preset frequency by using the output end, the receive end may receive the corresponding second electrical signal, and the intelligent device obtains the frequency of the second electrical signal by analyzing the second electrical signal received from the receive end. When the frequency of the second electrical signal matches the preset frequency, it indicates that the output end and the receive end of the intelligent device are in a connected mode, and it may be determined that the intelligent device is in a conducting liquid.

It may be understood that, that the frequency of the second electrical signal matches the frequency of the first electrical signal means that a difference between the frequency of the second electrical signal and the frequency of the first electrical signal is within an allowable range. In a possible example, the frequency of the second electrical signal matches the preset frequency, and it is required that a frequency difference between the frequency of the second electrical signal and the preset frequency is not greater than a preset frequency threshold. The preset frequency threshold is an allowable maximum frequency difference that is between the frequency of the second electrical signal and the preset frequency and that is set based on a specific situation. Generally, a value of the preset frequency threshold is very small, and may even be 0. When the preset frequency threshold is equal to 0, the frequency of the second electrical signal matches the preset frequency, and it is required that the frequency of the second electrical signal is equal to the preset frequency. A larger preset frequency threshold indicates a larger allowable maximum frequency difference between the frequency of the second electrical signal and the preset frequency.

For the condition 2, when the first sports characteristic data matches the preset sports characteristic data corresponding to the swimming mode, it indicates that a sports characteristic of a user wearing the intelligent device is consistent with a sports characteristic corresponding to swimming.

As an example, it is assumed that sports characteristic data corresponding to swimming postures such as butterfly, freestyle, breaststroke, and backstroke is prestored. That it is determined that the first sports characteristic data matches the preset sports characteristic data corresponding to the swimming mode may be as follows: The first sports characteristic data is analyzed. Specifically, sports characteristic data that is detected by an acceleration sensor and that indicates an acceleration change and sports characteristic data that is detected by a gyroscope apparatus and that indicates an angle change may be analyzed to obtain the sports characteristic data of the acceleration change and the sports characteristic data of the angle change. Then, a similarity between the sports characteristic data indicating the acceleration change and the sports characteristic data indicating the angle change, and prestored sports characteristic data corresponding to each swimming posture is calculated. When the similarity obtained through calculation is not less than a preset similarity threshold, it indicates that the first sports characteristic data matches the sports characteristic data corresponding to the swimming posture.

The preset similarity threshold is a minimum allowable similarity that is between the first sports characteristic data and standard sports characteristic data corresponding to each swimming posture and that is set based on a specific situation. When a similarity between the first sports characteristic data and preset sports characteristic data corresponding to a swimming posture is greater than or equal to the preset similarity threshold, it indicates that the intelligent device is currently in the swimming mode of this type. On the contrary, when a similarity between the first sports characteristic data and preset sports characteristic data corresponding to a swimming posture is less than the preset similarity threshold, it indicates that the intelligent device is currently not in the swimming mode of this type.

For example, it is assumed that the acceleration sensor and the gyroscope apparatus are integrated in the intelligent device, and the obtained first sports characteristic data includes the sports characteristic data AF1 indicating the acceleration change and the sports characteristic data GF1 indicating the angle change. Similarities between AF1 and GF1, and a prestored sports data characteristic SF1 of the butterfly, a prestored sports data characteristic SF2 of the freestyle, a prestored sports data characteristic SF3 of the breaststroke, and a prestored sports data characteristic SF4 of the backstroke are separately calculated. When a maximum value of a similarity is greater than the preset similarity threshold Th, to be specific, when max{f(SF1; AF1,GF1), f(SF2; AF1,GF1), f(SF3; AF1,GF1), f(SF3;AF1,GF1)}>Th in a mathematical form, it is determined that the user of the intelligent device is in the swimming mode, and the intelligent device enters the swimming mode. Otherwise, it is determined that the user is in another sports mode. f(A; B) is used to calculate a similarity between A and B.

It may be learned that in an embodiment, when a frequency of a signal sent by the output end matches a frequency of a signal received by the receive end, it may be determined that the intelligent device is currently in a liquid environment. This avoids a problem that the intelligent device makes a misjudgment on the swimming mode due to interference from factors such as static electricity, so that it can be accurately detected whether the intelligent device is in the liquid environment, and the intelligent device is enabled to accurately identify the swimming mode. Therefore, the intelligent device can accurately record and process swimming-related sports data for the user.

It may be understood that, after the intelligent device sets the sports mode to the swimming mode, to ensure that when the user exits a swimming sport, the intelligent device can accurately identify that the intelligent device is currently not in the swimming mode, and set the sports mode to a non-swimming mode, the method for setting a sports mode provided in this embodiment further includes how to accurately identify and set the non-swimming mode after the swimming mode.

In an embodiment, after operation 303, that is, after the intelligent device sets the sports mode to the swimming mode, this embodiment may further include: the intelligent device outputs a fifth electrical signal by using the output end and receives a sixth electrical signal by using the receive end; and the intelligent device sets the sports mode to the non-swimming mode if a frequency of the sixth electrical signal does not match a frequency of the fifth electrical signal.

In an embodiment, after the intelligent device sets the sports mode to the swimming mode, the intelligent device may receive and send signals between the output end and the receive end, to monitor in real time whether the intelligent device is continuously in the liquid environment. Once it is detected that the frequency of the sixth electrical signal received by the receive end does not match the frequency of the fifth electrical signal sent by the output end, it indicates that the intelligent device leaves the liquid environment, and therefore the intelligent device may switch the sports mode from the swimming mode to the non-swimming mode.

It should be noted that the fifth electrical signal may be the same as the first electrical signal, or may be different from the first electrical signal. Specifically, the frequency and/or an amplitude value of the fifth electrical signal may be the same as the frequency and/or an amplitude value of the first electrical signal, or may be different from the frequency and/or the amplitude value of the first electrical signal. For example, the fifth electrical signal may be a square wave signal. If the output end is connected to the receive end, that is, if the frequency of the sixth electrical signal matches the frequency of the fifth electrical signal, the sixth electrical signal may also be a square wave signal.

It may be learned that a moment at which the intelligent device leaves the liquid environment is accurately identified by determining whether a frequency of an electrical signal received by the receive end of the intelligent device matches a frequency of an electrical signal output by the output end, to switch the sports mode to the non-swimming mode, so that the intelligent device accurately identifies that the intelligent device exits the swimming mode.

In an embodiment, after operation 303, that is, after the intelligent device sets the sports mode to the swimming mode, this embodiment may further include: the intelligent device obtains second sports characteristic data detected by the sports sensing apparatus; and the intelligent device sets the sports mode to the non-swimming mode if the second sports characteristic data does not match the preset sports characteristic data.

In an embodiment, after the intelligent device sets the sports mode to the swimming mode, the intelligent device may monitor the second sports characteristic data of the intelligent device in real time by using the sports sensing apparatus, and perform similarity matching between the second sports characteristic data and the preset sports characteristic data corresponding to the swimming mode. Once it is detected that the second sports characteristic data collected by the sports sensing apparatus does not match the preset sports characteristic data, it indicates that the intelligent device does not perform the swimming sport, and therefore the intelligent device may switch the sports mode from the swimming mode to the non-swimming mode.

It should be noted that the second sports characteristic data may include: the sports characteristic data that is detected by the acceleration sensor and that indicates the acceleration change, and/or the sports characteristic data that is detected by the gyroscope apparatus and that indicates the angle change. For descriptions of the second sports characteristic data and an implementation of determining whether the second sports characteristic data matches the preset sports characteristic data, refer to the foregoing related descriptions of the first sports characteristic data. Details are not described herein again.

It may be learned that a moment at which the user corresponding to the intelligent device does not perform the swimming sport is accurately identified by determining whether sports characteristic data collected in real time by the sports sensing apparatus in the intelligent device matches the preset sports characteristic data, to switch the sports mode to the non-swimming mode, so that the intelligent device accurately identifies that the intelligent device exits the swimming mode.

It should be noted that the foregoing two implementations of setting the sports mode of the intelligent device to the non-swimming mode may both exist on the intelligent device, and are used as two optional modes for the user to select. If the first possible implementation is used to set the sports mode of the intelligent device to the non-swimming mode, because the sports mode is the swimming mode in all time periods in which the intelligent device is in the swimming environment, the intelligent device may collect all swimming data of the user in the swimming environment, and the collected swimming data is consecutive, comprehensive, and accurate. If the second possible implementation is used to set the sports mode of the intelligent device to the non-swimming mode, because the intelligent device is in the swimming environment, but switches to the non-swimming mode immediately when the swimming sport stops, the intelligent device collects only swimming data of the user in the swimming environment, and the collected swimming data is intermittent data. That is, only sports data of the user in the swimming sport is collected, and, the intelligent device may automatically exit the swimming mode and no longer collect swimming data at a moment at which the user rests in a swimming pool, thereby saving battery power of the intelligent device. In this implementation, the collected data may be independently collected to reflect data obtained when the user performs the swimming sport, and the user does not need to analyze and summarize, from all data, data that belongs to a swimming sports state.

In a possible scenario, the user wears the intelligent device to get out of the swimming environment, and after the swimming ends, the user no longer performs swimming in a short time (for example, within one hour). In this case, the user selects the first possible implementation or the second possible implementation as a manner of setting the sports mode to the non-swimming mode.

In another possible scenario, the user wears the intelligent device in the swimming environment, and needs to rest during swimming. In this case, to save resources (for example, battery power) of the intelligent device, the second possible implementation may be used as a manner of setting the sports mode to the non-swimming mode. In this way, when the user performs one time of swimming sport, the user may enter and exit the swimming mode for a plurality of times, and recorded swimming-related data is a set of sports data of a plurality of groups of swimming modes. In a time period in which the user rests in the swimming environment, the intelligent device exits the swimming mode and stops recording sports data. If resources (for example, battery power) of the intelligent device are adequate, the first possible implementation may be used as a manner of setting the sports mode to the non-swimming mode. In this way, when the user is in the swimming mode, swimming-related data is continuously recorded, the user does not stop recording sports data until the user gets out of the swimming environment, and all sports data of this swimming sport is collected.

In an embodiment, on a touch display screen of the intelligent device or on a terminal device connected to the intelligent device, the user may configure a specific manner of setting the non-swimming mode. In one case, the user may select, as a method to be performed by the intelligent device subsequently, one of the implementations of setting the sports mode of the intelligent device to the non-swimming mode. In another case, the user may select, as methods to be jointly performed by the intelligent device subsequently, the foregoing two implementations of setting the sports mode of the intelligent device to the non-swimming mode, and the sports mode of the intelligent device is set to the non-swimming mode once a condition of either implementation is met. In still another case, the user may select, as methods to be jointly performed by the intelligent device subsequently, the foregoing two implementations of setting the sports mode of the intelligent device to the non-swimming mode, and the sports mode of the intelligent device is set to the non-swimming mode only when conditions of the two implementations are both met.

It may be understood that the preset frequency, the preset sports characteristic data corresponding to the swimming mode, the setting condition of the swimming mode, and the like in this embodiment may all be fixed parameters that are provided and set by a system of the intelligent device before delivery or may be set, based on a requirement, by a skilled person or the user on the touch display screen of the intelligent device or on the terminal device connected to the intelligent device. This is not specifically limited herein.

According to the method for setting a sports mode provided in this embodiment, a problem that the intelligent device makes a misjudgment on the swimming mode due to interference from factors such as static electricity can be effectively avoided, and it can be accurately identified that the intelligent device enters the liquid environment, so that the intelligent device can accurately determine the swimming mode. In addition, after entering the swimming mode, the intelligent device may further accurately exit the swimming mode by identifying whether the intelligent device exits the liquid environment or whether the intelligent device exits the swimming sport, so that the intelligent device can automatically and accurately switch from the swimming mode to the non-swimming mode, thereby improving intelligence of the intelligent device and optimizing user experience.

Another embodiment of this application provides a method for setting a sports mode, which is different from the method in FIG. 3 in which electrical signals of a preset frequency are received and sent between a receive end and an output end to determine whether an intelligent device is in a liquid. In this embodiment, changes of the electrical signals received and sent between the receive end and the transmit end are detected, an impedance value between the receive end and the transmit end is calculated, and it is determined whether the impedance value is within a preset impedance range of water quality corresponding to a swimming mode, to determine whether the intelligent device is in a liquid environment suitable for swimming. In this way, a sports mode of the intelligent device is more accurately set.

Figure 4:
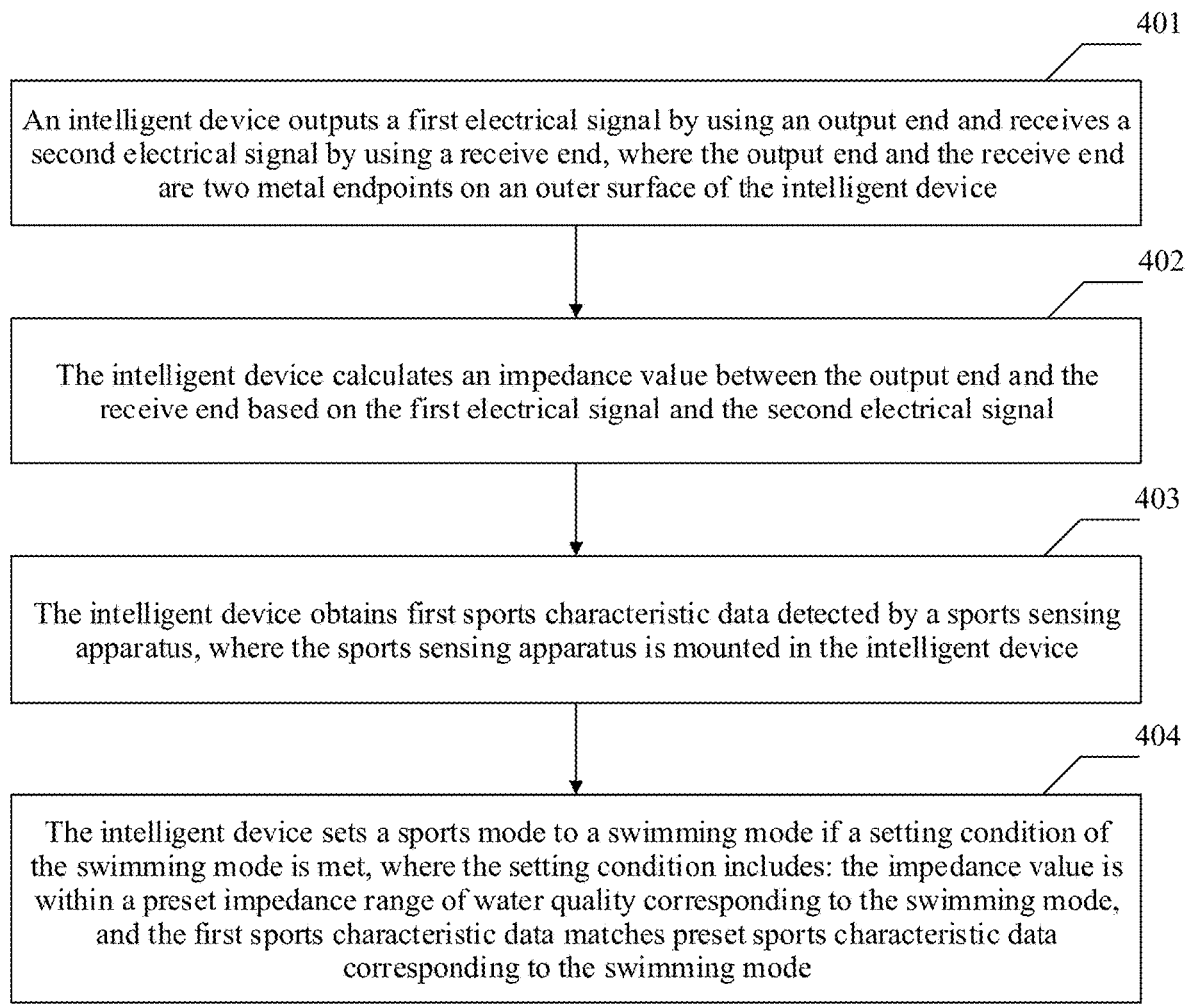
FIG. 4 is a schematic flowchart of another method for setting a sports mode according to an embodiment of this application.

Referring to FIG. 4, the method for setting a sports mode provided in this embodiment may include the following operations.

Operation 401: An intelligent device outputs a first electrical signal by using an output end and receives a second electrical signal by using a receive end, where the output end and the receive end are two metal endpoints on an outer surface of the intelligent device.

Operation 402: The intelligent device calculates an impedance value between the output end and the receive end based on the first electrical signal and the second electrical signal.

It may be understood that the two metal endpoints on the intelligent device are respectively used as the output end and the receive end of the intelligent device. After the output end outputs the first electrical signal, the receive end receives the second electrical signal. In an example, to simply generate and output the first electrical signal, the output end may select a direct-current signal that consumes fewer resources as the first electrical signal. In other words, the first electrical signal output by the output end may be a direct-current signal. If the receive end is connected to the output end, the second electrical signal received by the receive end may also be a direct-current signal.

If the intelligent device is in a liquid, that is, both the output end and the receive end are located in the liquid, because of conductivity of the liquid, a current path is formed among the receive end of the intelligent device, the liquid, and the output end. In this case, the impedance value between the output end and the receive end, namely, an impedance value of the liquid part, may be calculated based on the first electrical signal output by the output end and the second electrical signal received by the receive end.

In an embodiment, the calculating an impedance value between the output end and the receive end may be as follows: A voltage difference between the first electrical signal V1 and the second electrical signal V2 is calculated, that is, a voltage drop (V1−V2) generated when a current on the current path flows through the liquid part is obtained. A reference current of the receive end is calculated by using a known reference resistance R of the receive end, and specifically, the reference current (V2/R) of the receive end, namely, a current value on the entire current path, may be obtained by dividing the second electrical signal V2 by the reference resistance R of the receive end. Finally, the voltage difference obtained through calculation is divided by the reference current of the receive end, to be specific, (V1−V2)/(V2/R), to obtain the impedance value between the output end and the receive end, namely, the impedance value of the liquid in which the intelligent device is located.

It may be learned that in an embodiment, the impedance value between the receive end and the output end is obtained through calculation by receiving and sending electrical signals between the metal endpoints on the surface of the intelligent device, and a calculation result may represent the impedance value of the liquid in which the intelligent device is located. In this way, water quality in which the intelligent device is located is accurately determined, so that a sports mode can be accurately set subsequently.

Operation 403: The intelligent device obtains first sports characteristic data detected by a sports sensing apparatus, where the sports sensing apparatus is mounted in the intelligent device.

The sports sensing apparatus may include an acceleration sensor and/or a gyroscope apparatus. The acceleration sensor is configured to detect sports characteristic data indicating an acceleration change, and the gyroscope apparatus is configured to detect sports characteristic data indicating an angle change.

For descriptions of the first sports characteristic data and a specific implementation of operation 403, refer to the specific implementation of operation 202 in the embodiment shown in FIG. 2 and the specific implementation of operation 302 in the embodiment shown in FIG. 3. Details are not described herein again.

It should be noted that there is no limitation on a sequence of performing operations 401 and 402 and operation 403. Operations 401 and 402 may be performed before operation 403, or operation 403 may be performed before operations 401 and 402, or operations 401 and 402 and operation 403 may be performed at the same time. This is not specifically limited herein.

Operation 404: The intelligent device sets a sports mode to a swimming mode if a setting condition of the swimming mode is met, where the setting condition includes: the impedance value is within a preset impedance range of water quality corresponding to the swimming mode, and the first sports characteristic data matches preset sports characteristic data corresponding to the swimming mode.

It may be determined, based on the impedance value between the receive end and the output end that is obtained through calculation in operation 402 and the first sports characteristic data detected by the sports sensing apparatus of the intelligent device in operation 403, whether the intelligent device currently meets the preset setting condition of the swimming mode. The setting condition of the swimming mode includes but is not limited to the following: Condition 1: The impedance value obtained through calculation is within the preset impedance range of the water quality corresponding to the swimming mode. Condition 2: The first sports characteristic data matches the preset sports characteristic data corresponding to the swimming mode. When both the condition 1 and the condition 2 are met, it indicates that the intelligent device is currently in the swimming mode. In this case, the intelligent device sets the sports mode to the swimming mode, so that the intelligent device can accurately record and process swimming-related sports data for a user.

For the condition 1, after the impedance value between the output end and the receive end is obtained through calculation, the intelligent device may compare the impedance value with the preset impedance range of the water quality corresponding to the preset swimming mode. Once the impedance value is within one of preset impedance ranges, it indicates that an environment in which the intelligent device is currently located is a liquid suitable for swimming (for example, pool water of a swimming hall or sea water), and it may be further determined that the intelligent device is in the water quality corresponding to the swimming mode.

It may be understood that, the water quality corresponding to the swimming mode is water quality suitable for swimming, for example, pool water of a swimming hall or sea water. The preset impedance range of the water quality corresponding to the swimming mode is a set of preset impedance values of each type of water quality corresponding to the swimming mode. It is assumed that the water quality corresponding to the swimming mode includes standard pool water of a swimming hall and sea water, a preset impedance range [a, b] of the standard pool water of the swimming hall is obtained, and a preset impedance range [c, d] of the standard pool water of the swimming hall is obtained. In this case, a preset impedance range of the preset impedance range of the water quality corresponding to the swimming mode is $\{[a,b], [c,d]\}$. Once an impedance value x between the receive end and the output end that is obtained through calculation belongs to [a, b] or [c, d], it indicates that the impedance value is within the preset impedance range of the water quality corresponding to the swimming mode, and the condition 1 is met.

For descriptions and an implementation of the condition 2, refer to the descriptions of the condition 2 in operation 203 and operation 303. Details are not described herein again.

It may be learned that, in this embodiment, the impedance value between the two metal endpoints of the current intelligent device, namely, an impedance value of the environment in which the intelligent device is currently located, may be calculated by obtaining a signal sent by the output end and a signal received by the receive end, to compare the impedance value with the preset impedance range of the water quality corresponding to the swimming mode, and accurately determine whether the current environment is an environment in which water quality is suitable for swimming, namely, a swimming environment. When the impedance value obtained through calculation is within a preset impedance range corresponding to the swimming environment, it may be determined that the intelligent device is in the swimming environment, so that the intelligent device automatically enters the swimming mode. This avoids a problem that the intelligent device incorrectly switches to the swimming mode when the intelligent device is in a non-swimming liquid environment, and enables the intelligent device to more accurately identify the swimming mode. Therefore, the intelligent device can accurately record and process swimming-related sports data for a user.

It may be understood that, after the intelligent device sets the sports mode to the swimming mode, to ensure that when the user exits a swimming sport, the intelligent device can accurately identify that the intelligent device is currently not in the swimming mode, and set the sports mode to a non-swimming mode, the method for setting a sports mode provided in this embodiment further includes how to accurately identify and set the non-swimming mode after the swimming mode.

In an embodiment, after operation 404, that is, after the intelligent device sets the sports mode to the swimming mode, this embodiment may further include: the intelligent device obtains second sports characteristic data detected by the sports sensing apparatus; and the intelligent device sets the sports mode to the non-swimming mode if the second sports characteristic data does not match the preset sports characteristic data.

In an embodiment, after the intelligent device sets the sports mode to the swimming mode, the intelligent device may monitor the second sports characteristic data of the intelligent device in real time by using the sports sensing apparatus, and perform similarity matching between the second sports characteristic data and the preset sports characteristic data corresponding to the swimming mode. Once it is detected that the second sports characteristic data collected by the sports sensing apparatus does not match the preset sports characteristic data, it indicates that the intelligent device does not perform the swimming sport, and therefore the intelligent device may switch the sports mode from the swimming mode to the non-swimming mode.

It should be noted that the second sports characteristic data may include: the sports characteristic data that is detected by the acceleration sensor and that indicates the acceleration change, and/or the sports characteristic data that is detected by the gyroscope apparatus and that indicates the angle change. For descriptions of the second sports characteristic data and an implementation of determining whether the second sports characteristic data matches the preset sports characteristic data, refer to the foregoing related descriptions of the first sports characteristic data. Details are not described herein again.

It may be learned that a moment at which the user corresponding to the intelligent device does not perform the swimming sport is accurately identified by determining whether sports characteristic data collected in real time by the sports sensing apparatus in the intelligent device matches the preset sports characteristic data, to switch the sports mode to the non-swimming mode, so that the intelligent device accurately identifies that the intelligent device exits the swimming mode.

It should be noted that, the preset sports characteristic data corresponding to the swimming mode, the preset impedance range of the water quality corresponding to the swimming mode, the setting condition of the swimming mode, and the like in the foregoing embodiment may all be fixed parameters that are provided and set by a system of the intelligent device or may be preset by a skilled person or the user on a touch display screen of the intelligent device or on a terminal device connected to the intelligent device before swimming. This is not specifically limited herein.

Therefore, according to the method for setting a sports mode provided in this embodiment, the impedance value between the two the metal endpoints of the current intelligent device may be calculated, to accurately determine whether the current environment is an environment in which water quality is suitable for swimming, namely, the swimming environment. This avoids a problem that the intelligent device incorrectly switches the sports mode when the intelligent device is in a non-swimming liquid environment, and enables the intelligent device to more accurately identify the swimming mode. In addition, after entering the swimming mode, the intelligent device may further accurately exit the swimming mode by identifying whether the intelligent device exits the swimming sport, so that the intelligent device can automatically and accurately switch from the swimming mode to the non-swimming mode, thereby improving intelligence of the intelligent device and optimizing user experience.

To further implement accurate setting of a sports mode by an intelligent device and implement automatic and accurate switching between a swimming mode and a non-swimming mode, an embodiment of this application further provides a method for setting a sports mode. The method for setting a sports mode may be combined with the methods shown in FIG. 3 and FIG. 4 to perform double determining on an environment in which the intelligent device is located, thereby providing a more accurate data basis for setting a sports mode of the intelligent device.

Figure 5:
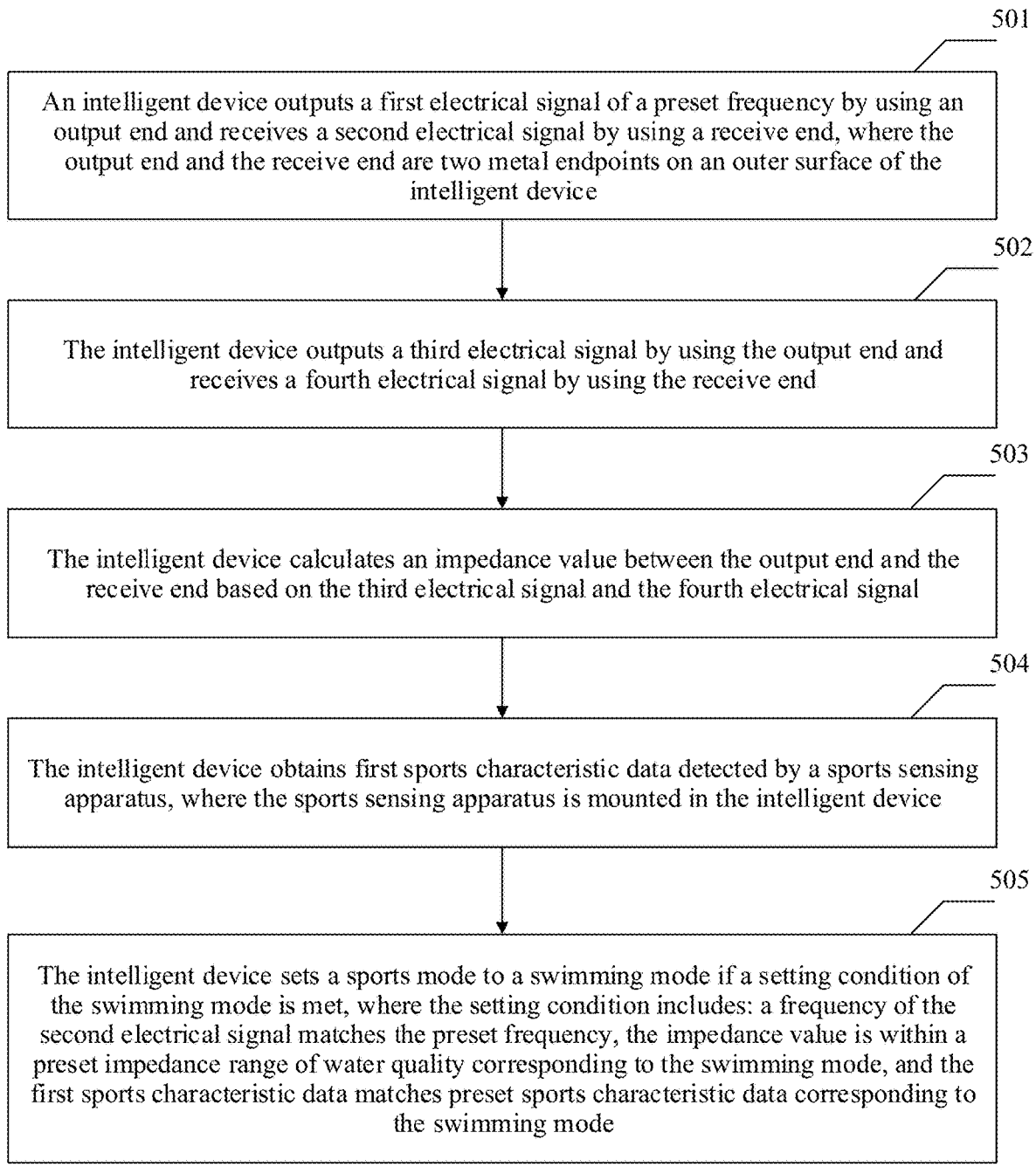
FIG. 5 is a schematic flowchart of still another method for setting a sports mode according to an embodiment of this application.

Referring to FIG. 5, the method for setting a sports mode provided in this embodiment may include the following operations.

Operation 501: An intelligent device outputs a first electrical signal of a preset frequency by using an output end and receives a second electrical signal by using a receive end, where the output end and the receive end are two metal endpoints on an outer surface of the intelligent device.

During specific implementation, the first electrical signal and the second electrical signal may be square wave signals.

It may be understood that, for descriptions and a specific implementation of operation 501, refer to the descriptions of operation 301 in the embodiment shown in FIG. 3. Details are not described herein again.

Operation 502: The intelligent device outputs a third electrical signal by using the output end and receives a fourth electrical signal by using the receive end.

Operation 503: The intelligent device calculates an impedance value between the output end and the receive end based on the third electrical signal and the fourth electrical signal.

In an embodiment, the third electrical signal and the fourth electrical signal may be direct-current signals.

It may be understood that, for descriptions and specific implementations of operations 502 and 503, refer to the descriptions of operations 401 and 402 in the embodiment shown in FIG. 4. Details are not described herein again.

Operation 504: The intelligent device obtains first sports characteristic data detected by a sports sensing apparatus, where the sports sensing apparatus is mounted in the intelligent device.

It may be understood that, for descriptions and a specific implementation of operation 504, refer to the descriptions of operation 202 in the embodiment shown in FIG. 2, or refer to the descriptions of operation 302 in the embodiment shown in FIG. 3, or refer to the descriptions of operation 403 in the embodiment shown in FIG. 4. Details are not described herein again.

It should be noted that there is no limitation on a sequence of performing operation 501, operations 502 and 503, and operation 504. This is not specifically limited herein.

Operation 505: The intelligent device sets a sports mode to a swimming mode if a setting condition of the swimming mode is met, where the setting condition includes: a frequency of the second electrical signal matches the preset frequency, the impedance value is within a preset impedance range of water quality corresponding to the swimming mode, and the first sports characteristic data matches preset sports characteristic data corresponding to the swimming mode.

It may be determined, based on the second electrical signal received by the receive end of the intelligent device in operation 501, the impedance value between the receive end and the output end that is obtained through calculation in operation 503, and the first sports characteristic data detected by the sports sensing apparatus of the intelligent device in operation 504, whether the intelligent device currently meets the preset setting condition of the swimming mode. The setting condition of the swimming mode includes but is not limited to the following: Condition 1: The frequency of the second electrical signal matches the preset frequency. Condition 2: The impedance value obtained through calculation is within the preset impedance range of the water quality corresponding to the swimming mode. Condition 3: The first sports characteristic data matches the preset sports characteristic data corresponding to the swimming mode.

For descriptions and an implementation of the condition 1, refer to the descriptions of the condition 1 in operation 303. Details are not described herein again.

For descriptions and an implementation of the condition 2, refer to the descriptions of the condition 1 in operation 404. Details are not described herein again.

For descriptions and an implementation of the condition 3, refer to the descriptions of the condition 2 in operation 203, operation 303, and operation 404. Details are not described herein again.

When the condition 1, the condition 2, and the condition 3 are all met, it indicates that the intelligent device is currently in the swimming mode. In this case, the intelligent device sets the sports mode to the swimming mode, so that the intelligent device can accurately record and process swimming-related sports data for a user.

It may be learned that, in an embodiment, when it may be determined, by sending and receiving electrical signals of the preset frequency, that the intelligent device is currently in a liquid environment, the impedance value between the two metal endpoints of the current intelligent device may be further calculated, to compare the impedance value with the preset impedance range of the water quality corresponding to the swimming mode, and accurately determine whether the current liquid environment is a liquid environment suitable for swimming, namely, a swimming environment. The intelligent device can automatically enter the swimming mode only when it is determined that the intelligent device is in the liquid environment and the liquid environment is the swimming environment. This avoids a problem that the intelligent device incorrectly switches to the swimming mode when the intelligent device is in a non-swimming liquid environment. In addition, a problem that the intelligent device makes a misjudgment on the swimming mode due to interference from factors such as static electricity is overcome, and the intelligent device is enabled to more accurately identify the swimming mode. Therefore, the intelligent device can accurately enter the swimming mode, and record and process swimming-related sports data for a user.

It may be understood that, after the intelligent device sets the sports mode to the swimming mode, to ensure that when the user exits a swimming sport, the intelligent device can accurately identify that the intelligent device is currently not in the swimming mode, and set the sports mode to a non-swimming mode, the method for setting a sports mode provided in this embodiment further includes how to accurately identify and set the non-swimming mode after the swimming mode.

In an embodiment, after operation 505, that is, after the intelligent device sets the sports mode to the swimming mode, this embodiment may further include: the intelligent device outputs a fifth electrical signal of the preset frequency by using the output end and receives a sixth electrical signal by using the receive end; and the intelligent device sets the sports mode to the non-swimming mode if a frequency of the sixth electrical signal does not match the preset frequency of the fifth electrical signal.

In another embodiment, after operation 505, that is, after the intelligent device sets the sports mode to the swimming mode, this embodiment may further include: the intelligent device obtains second sports characteristic data detected by the sports sensing apparatus; and the intelligent device sets the sports mode to the non-swimming mode if the second sports characteristic data does not match the preset sports characteristic data.

For specific descriptions of the foregoing two possible implementations, refer to the corresponding descriptions of the implementation of how to exit the swimming mode in the embodiment shown in FIG. 3. Details are not described herein again.

It should be noted that, in the foregoing implementation of switching from the swimming mode to the non-swimming mode, the fifth electrical signal of the preset frequency and the sixth electrical signal are used in the embodiments shown in FIG. 3 and FIG. 5, because the fifth electrical signal and the sixth electrical signal are consecutive signals and are relatively stable and reliable to monitor whether the intelligent device is still in the swimming mode. However, in the embodiments shown in FIG. 4 and FIG. 5, the manner of calculating the impedance value is not used to determine whether the user corresponding to the intelligent device exits the swimming mode, because the calculation of the impedance value is an unreliable implementation for leaving from the liquid environment. Even if the user leaves from the liquid environment, there may be a liquid between the input end and the receive end, and the sports mode of the intelligent device is likely to be misjudged. Sports characteristic data detected by the sports sensing apparatus may be used in all the embodiments shown in FIG. 3, FIG. 4, and FIG. 5, because once the sports characteristic data does not match the preset sports characteristic data corresponding to the swimming mode, it may be directly indicated that the user corresponding to the intelligent device has exited the swimming mode. This manner is relatively intuitive and accurate.

After the methods for setting a sports mode shown in FIG. 3, FIG. 4, and FIG. 5 are described, to make the methods provided in the embodiments of this application clearer and more vivid, the following describes an effect of setting, by the intelligent device, the sports mode of the intelligent device shown in FIG. 1 to the swimming mode.

Figure 6:
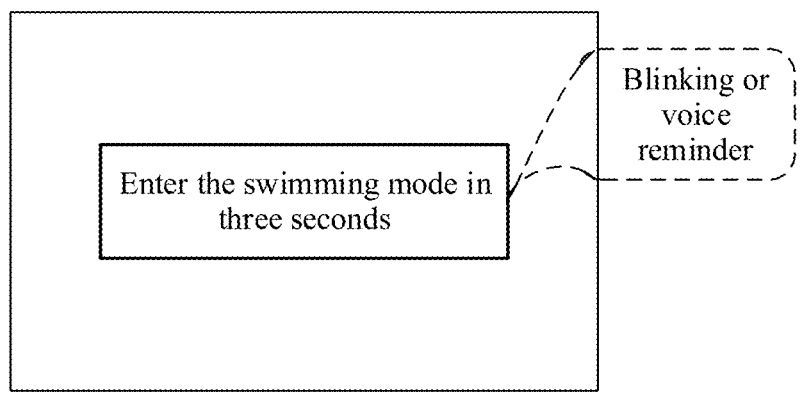
FIG. 6 is a schematic effect diagram of setting a sports mode according to an embodiment of this application.
Figure 7:
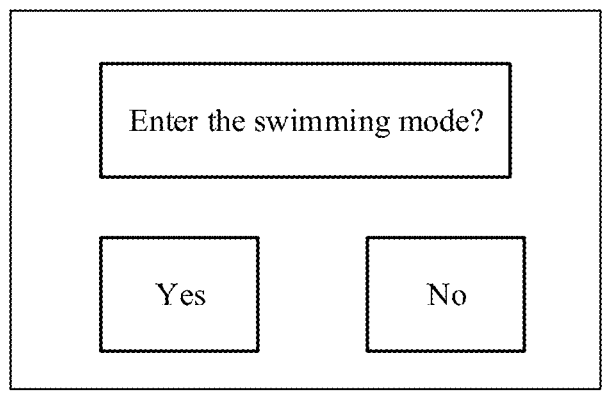
FIG. 7 is another schematic effect diagram of setting a sports mode according to an embodiment of this application.

It may be understood that, to improve user experience, after it is determined that the current intelligent device meets the setting condition of the swimming mode, a pop-up prompt window shown in FIG. 6 may be displayed on a display apparatus, including on a touch display screen of the intelligent device or on a terminal device connected to the intelligent device, to prompt the user to "Enter the swimming mode in three seconds" in a form of blinking or a voice reminder. To improve accuracy of switching the sports mode, prompt information shown in FIG. 7 may be further displayed on the display apparatus, including on the touch display screen of the intelligent device or on the terminal device connected to the intelligent device. The user needs to confirm whether to "Enter the swimming mode", and when the user selects "Yes" within a preset time (for example, three seconds) or does not select "No" within the preset time, the intelligent device enters the swimming mode.

Likewise, when identifying that the user currently exits the swimming mode, the intelligent device may also pop up the prompt information on the touch display screen of the intelligent device or on the terminal device connected to the intelligent device, so that the user determines "Whether to exit the swimming mode", to further improve accuracy of setting the sports mode.

It should be noted that the intelligent device may have all the three detection methods for detecting that the user enters the swimming mode shown in FIG. 3, FIG. 4, and FIG. 5. After the user selects a detection method by using the touch display screen of the intelligent device or by using the terminal device connected to the intelligent device, the intelligent device may detect the sports mode of the user according to the detection method selected by the user, and set the sports mode of the user based on a detection result. For example, assuming that the user selects the method for setting a sports mode shown in FIG. 3 on the terminal device connected to the intelligent device, the intelligent device sets the sports mode of the intelligent device according to the method shown in FIG. 3.

To make the method for setting a sports mode provided in this embodiment of this application clearer, the following describes, by using a specific scenario, the method for setting a sports mode. Assuming that the intelligent device is a sports bracelet, an interface that is on the sports bracelet and that is used for charging includes two metal endpoints, and the two metal endpoints may be used as an output end and a receive end of signals. The sports bracelet has a touch display screen. The sports bracelet is integrated with a sports sensing apparatus, including an acceleration sensor and a gyroscope apparatus. In addition, the sports bracelet may be connected to a corresponding mobile phone APP in a manner such as Bluetooth.

Figure 8A:
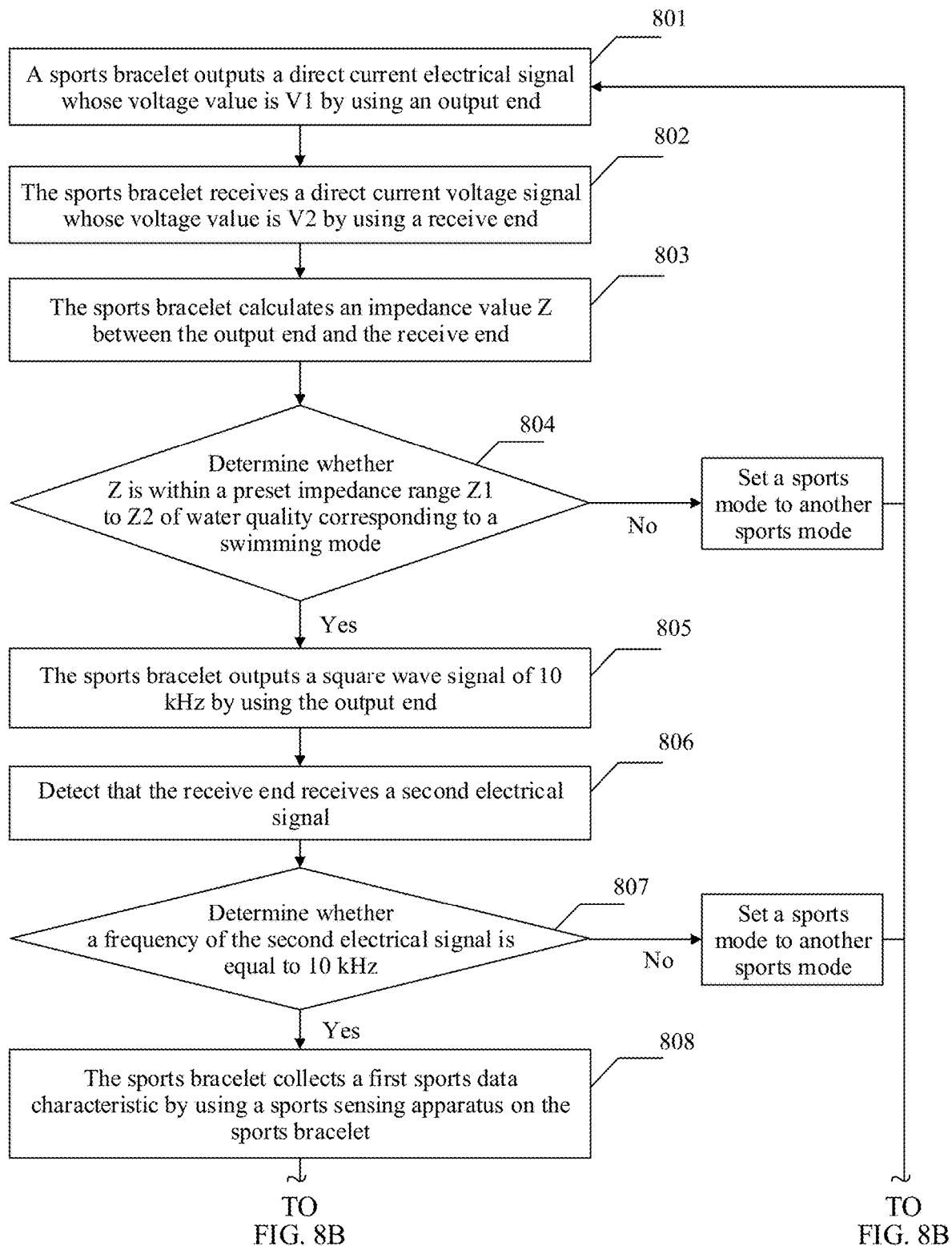
FIG. 8A and FIG. 8B are a schematic diagram of an example of a method for setting a sports mode according to an embodiment of this application.
Figure 8B:
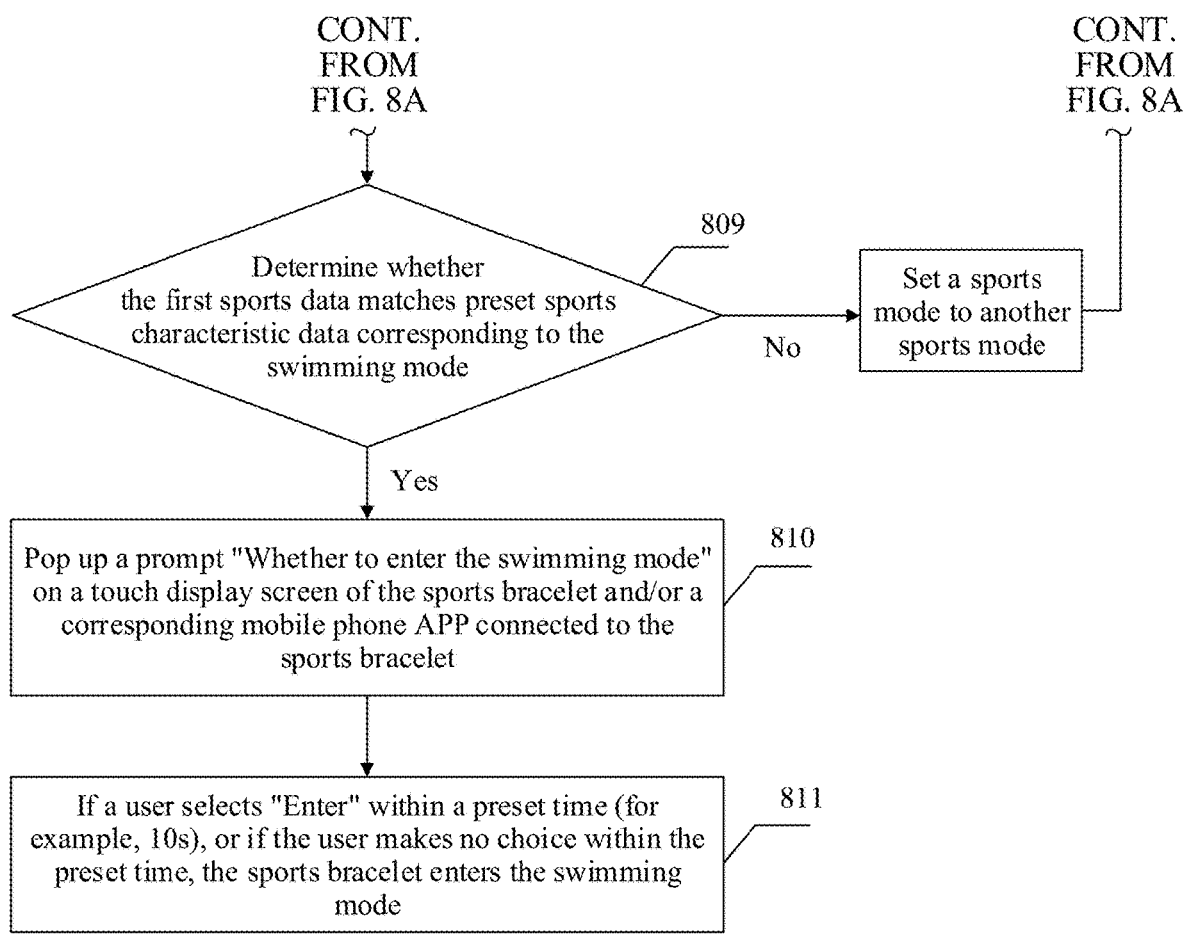

FIG. 8A and FIG. 8B are a schematic flowchart of a method for setting a sports mode according to an embodiment of this application. In this embodiment, when a user wears a sports bracelet to go to a swimming hall for swimming and enters a swimming pool from the land, the method may include the following operations.

Operation 801: A sports bracelet outputs a direct-current electrical signal whose voltage value is V1 by using an output end.

Operation 802: The sports bracelet receives a direct-current voltage signal whose voltage value is V2 by using a receive end.

Operation 803: The sports bracelet calculates an impedance value Z between the output end and the receive end.

During specific implementation, if a reference resistance of the receive end is R, it can be known that Z=(V1−V2)/(V2/R) based on basic knowledge of a circuit.

Operation 804: Determine whether Z is within a preset impedance range Z1 to Z2 of water quality corresponding to a swimming mode, and perform operation 805 if yes; otherwise, set a sports mode to another sports mode, and continue to perform operation 801.

Operation 805: The sports bracelet outputs a square wave signal of 10 kHz by using the output end.

Operation 806: Detect that the receive end receives an electrical signal.

Operation 807: Determine whether a frequency of a second electrical signal is equal to 10 kHz, and perform operation 808 if yes; otherwise, set a sports mode to another sports mode, and continue to perform operation 801.

Operation 808: The sports bracelet collects a first sports data characteristic by using a sports sensing apparatus on the sports bracelet.

It may be understood that the first sports data characteristic includes sports characteristic data AF1 indicating an acceleration change and sports characteristic data GF1 indicating an angle change.

Operation 809: Determine whether the first sports data matches preset sports characteristic data corresponding to the swimming mode, and perform operation 810 if yes; otherwise, set a sports mode to another sports mode, and continue to perform operation 801.

Operation 810: Pop up a prompt "Whether to enter the swimming mode" on a touch display screen of the sports bracelet and/or a corresponding mobile phone APP connected to the sports bracelet.

Operation 811: If a user selects "Yes" within a preset time (for example, 10 s), or if the user makes no choice within the preset time, the sports bracelet enters the swimming mode.

Figure 9:
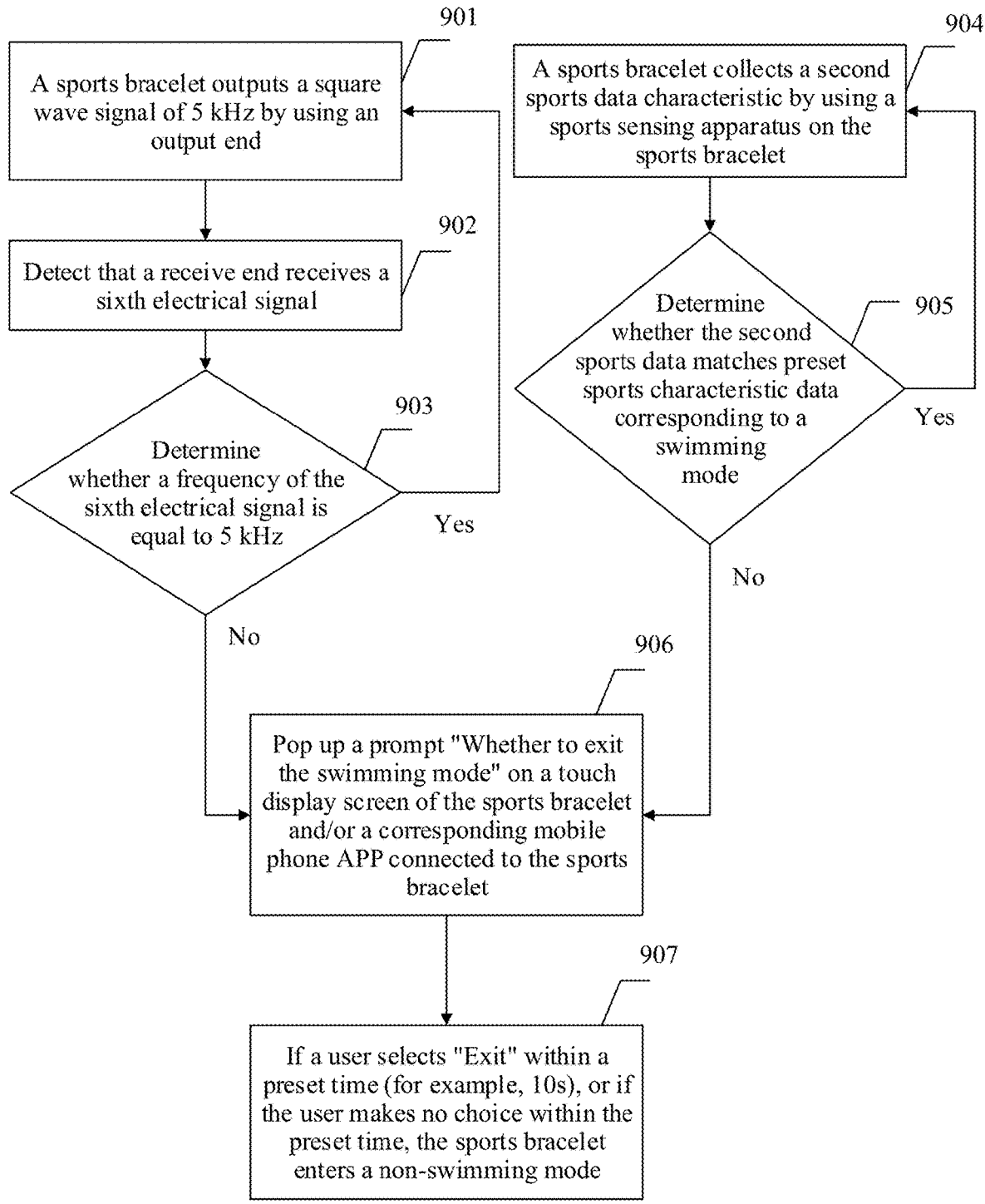
FIG. 9 is a schematic diagram of another example of a method for setting a sports mode according to an embodiment of this application.

After the sports bracelet enters the swimming mode, in this embodiment, when the user wears the sports bracelet from pool water to the land, referring to FIG. 9, the method may include the following operations.

Operation 901: A sports bracelet outputs a square wave signal of 5 kHz by using an output end.

Operation 902: Detect that a receive end receives an electrical signal.

The output end and the receive end are two metal endpoints on an outer surface of an intelligent device.

Operation 903: Determine whether a frequency of a sixth electrical signal is equal to 5 kHz, and perform operation 906 if no; otherwise, continue to perform operation 901 to operation 903.

Alternatively, the method may include the following operations.

Operation 904: A sports bracelet collects a second sports data characteristic by using a sports sensing apparatus on the sports bracelet.

Operation 905: Determine whether the second sports data matches preset sports characteristic data corresponding to a swimming mode, and perform operation 906 if no; otherwise, perform operations 904 and 905.

Operation 906: Pop up a prompt "Whether to exit the swimming mode" on a touch display screen of the sports bracelet and/or a corresponding mobile phone APP connected to the sports bracelet.

Operation 907: If a user selects "Exit" within a preset time (for example, 10 s), or if the user makes no choice within the preset time, the sports bracelet enters a non-swimming mode.

It should be noted that, in both the method of operations 901 to 903 and the method of operations 904 and 905, it may be independently determined that the user is no longer in a swimming state. Specifically, whether to use the manner of operations 901 to 903 or the manner of operations 904 and 905 may be set at delivery of the sports bracelet, or may be preset by the user or a skilled person on the touch display screen of the sports bracelet or on the mobile phone APP connected to the sports bracelet. This is not specifically limited herein.

According to the method for setting a sports mode provided in an embodiment, an impedance value between the two metal endpoints of the intelligent device such as the current sports bracelet may be calculated to accurately determine whether a current environment is an environment in which water quality is suitable for swimming, namely, a swimming environment. This avoids a problem that the intelligent device incorrectly switches a sports mode when the intelligent device is in a non-swimming liquid environment, and enables the intelligent device to more accurately identify the swimming mode. In addition, after entering the swimming mode, the intelligent device may further accurately exit the swimming mode by identifying whether the intelligent device exits a swimming sport, so that the intelligent device can automatically and accurately switch from the swimming mode to a non-swimming mode, thereby improving intelligence of the intelligent device and optimizing user experience.

Figure 10:
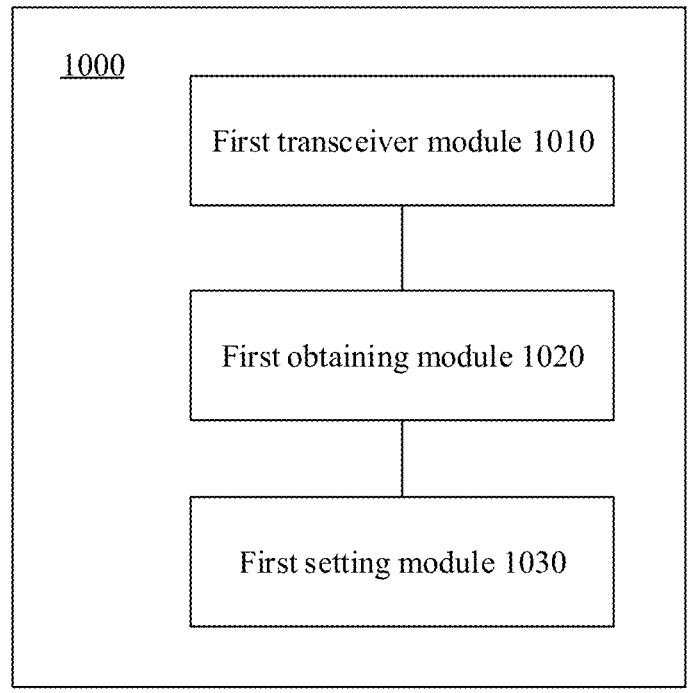
FIG. 10 is a schematic structural diagram of an intelligent device for setting a sports mode according to an embodiment of this application.

In addition, an embodiment of this application further provides an intelligent device for setting a sports mode. FIG. 10 is a schematic structural diagram of an intelligent device for setting a sports mode according to an embodiment of this application. The intelligent device 1000 may include the following modules.

A first transceiver module 1010 is configured to: output a first electrical signal by using an output end and receive a second electrical signal by using a receive end, where the output end and the receive end are two metal endpoints on an outer surface of the intelligent device. For example, the first transceiver module 1010 may be configured to perform the method in operation 201. For details, refer to the description of operation 201 in the method embodiment. Details are not described herein again.

A first obtaining module 1020 is configured to obtain first sports characteristic data detected by a sports sensing apparatus, where the sports sensing apparatus is mounted in the intelligent device. For example, the first obtaining module 1020 may be configured to perform the method in operation 202. For details, refer to the description of operation 202 in the method embodiment. Details are not described herein again.

A first setting module 1030 is configured to set a sports mode to a swimming mode if a setting condition of the swimming mode is met, where the setting condition includes: a variation between the second electrical signal and the first electrical signal meets a preset condition, and the first sports characteristic data matches preset sports characteristic data corresponding to the swimming mode. For example, the first setting module 1030 may be configured to perform the method in operation 203. For details, refer to the description of operation 203 in the method embodiment. Details are not described herein again.

Therefore, in this embodiment of this application, the intelligent device 1000 for setting a sports mode may use the two metal endpoints on the outer surface of the intelligent device respectively as the output end and the receive end of signals. A signal sent by the output end is compared with a signal received by the receive end to determine whether the intelligent device currently meets the preset condition, and also to determine whether the first sports characteristic data matches the preset sports characteristic data corresponding to the swimming mode. When two determining results are both "yes", it can be determined that the intelligent device meets the setting condition of the swimming mode, or in other words, the intelligent device is enabled to accurately identify and set the swimming mode. Therefore, the intelligent device can accurately record and process swimming-related sports data for a user.

In an embodiment, the preset condition is: a frequency of the second electrical signal matches a frequency of the first electrical signal.

In an embodiment, the first electrical signal and the second electrical signal are square wave signals.

It may be learned that, in an embodiment of this application, the intelligent device 1000 for setting a sports mode may use the two metal endpoints on the outer surface of the intelligent device respectively as the output end and the receive end of signals. A signal sent by the output end is compared with a signal received by the receive end to determine whether the intelligent device is currently in a liquid environment. When a frequency of the signal sent by the output end matches a frequency of the signal received by the receive end, it can be determined that the intelligent device is currently in the liquid environment. This can avoid a problem that the intelligent device makes a misjudgment on the swimming mode due to interference from factors such as static electricity, so that it can be accurately detected whether the intelligent device is in the liquid environment, and the intelligent device is enabled to accurately identify and set the swimming mode. Therefore, the intelligent device can accurately record and process swimming-related sports data for a user.

In an embodiment, the intelligent device 1000 further includes:

a second transceiver module, configured to: output a third electrical signal by using the output end and receive a fourth electrical signal by using the receive end; and a calculation module, configured to calculate an impedance value between the output end and the receive end based on the third electrical signal and the fourth electrical signal, where correspondingly, the setting condition further includes: the impedance value is within a preset impedance range.

In an embodiment, the third electrical signal and the fourth electrical signal are direct-current signals.

In an embodiment, the preset condition is: an impedance value between the output end and the receive end that is calculated based on the first electrical signal and the second electrical signal is within a preset impedance range.

It may be learned that, in an embodiment of this application, the intelligent device 1000 for setting a sports mode may, by obtaining a signal sent by the output end and a signal received by the receive end, calculate an impedance value between the two metal endpoints of the current intelligent device, namely, an impedance value of a environment in which the intelligent device is currently located, to compare the impedance value with the preset impedance range of water quality corresponding to the swimming mode, and accurately determine whether the current liquid environment is a liquid environment corresponding to the swimming mode, namely, a swimming environment. When the impedance value obtained through calculation is within the preset impedance range corresponding to the swimming environment, it can be determined that the intelligent device is in the swimming environment, so that the intelligent device automatically enters the swimming mode. This avoids a problem that the intelligent device incorrectly switches to the swimming mode when the intelligent device is in a non-swimming liquid environment, and enables the intelligent device to more accurately identify the swimming mode. Therefore, the intelligent device can accurately record and process swimming-related sports data for a user.

In an embodiment, the sports sensing apparatus includes an acceleration sensor and/or a gyroscope apparatus. The acceleration sensor is configured to detect sports characteristic data indicating an acceleration change, and the gyroscope apparatus is configured to detect sports characteristic data indicating an angle change.

In an embodiment, after the intelligent device sets the sports mode to the swimming mode, the intelligent device 1000 further includes:

a third transceiver module, configured to: output a fifth electrical signal by using the output end and receive a sixth electrical signal by using the receive end; and a second setting module, configured to set the sports mode to a non-swimming mode if a frequency of the sixth electrical signal does not match a frequency of the fifth electrical signal.

In an embodiment, after the intelligent device sets the sports mode to the swimming mode, the intelligent device 1000 further includes:

a second obtaining module, configured to obtain second sports characteristic data detected by the sports sensing apparatus; and a third setting module, configured to set the sports mode to the non-swimming mode if the second sports characteristic data does not match the preset sports characteristic data.

It may be learned that, the intelligent device 1000 for setting a sports mode provided in this embodiment of this application can accurately identify and set the swimming mode. In addition, after entering the swimming mode, the intelligent device may further accurately exit the swimming mode by identifying whether the intelligent device exits the swimming sport, so that the intelligent device can automatically and accurately switch from the swimming mode to the non-swimming mode, thereby improving intelligence of the intelligent device and optimizing user experience.

Figure 11:
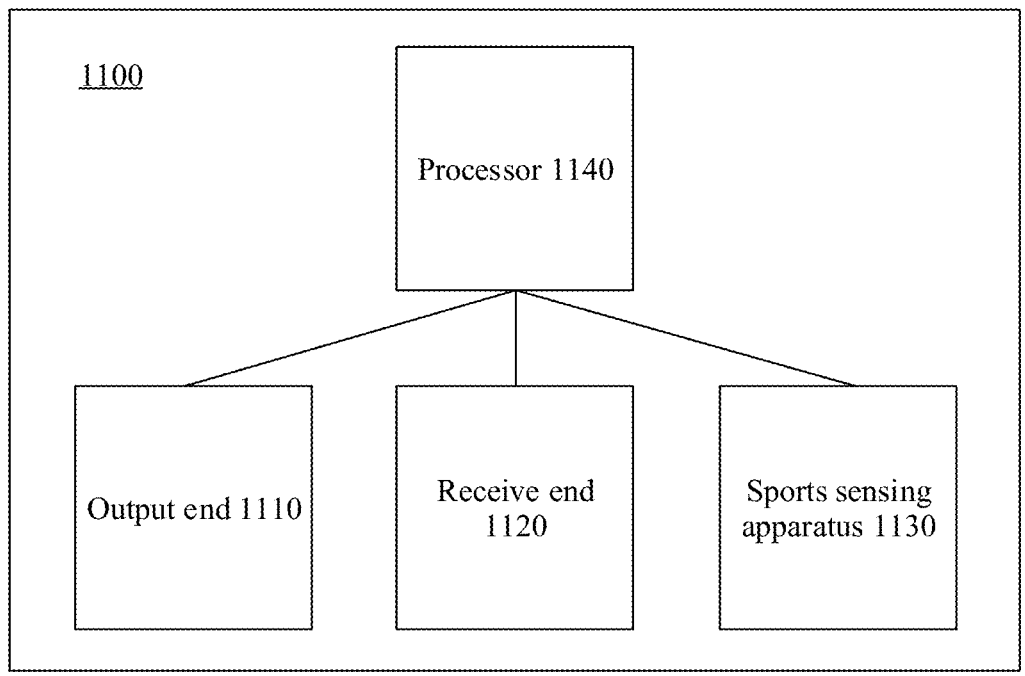
FIG. 11 is a schematic diagram of an intelligent device for setting a sports mode according to an embodiment of this application.

In addition, an embodiment of this application further provides an intelligent device for setting a sports mode. FIG. 11 is a schematic diagram of an intelligent device according to an embodiment of this application. The intelligent device 1100 includes an output end 1110, a receive end 1120, a sports sensing apparatus 1130, and a processor 1140.

The processor 1140 is configured to: read a software instruction in a memory, and execute the software instruction to implement the following operations:

driving the output end 1110 to output a first electrical signal and driving the receive end 1120 to receive a second electrical signal, where the output end 1110 and the receive end 1120 are two metal endpoints on an outer surface of the intelligent device;

driving the sports sensing apparatus 1130 to detect first sports characteristic data, where the sports sensing apparatus 1130 is mounted in the intelligent device; and setting a sports mode to a swimming mode if a setting condition of the swimming mode is met, where the setting condition includes: a variation between the second electrical signal and the first electrical signal meets a preset condition, and the first sports characteristic data matches preset sports characteristic data corresponding to the swimming mode.

For details, refer to the descriptions of operation 201 to operation 203. Details are not described herein again.

In an embodiment, the preset condition is: a frequency of the second electrical signal matches a frequency of the first electrical signal.

In an embodiment, the first electrical signal and the second electrical signal are square wave signals.

In an embodiment, the processor 1140 is configured to: read a software instruction in the memory, and further execute the software instruction to implement the following operations:

driving the output end to output a third electrical signal and driving the receive end to receive a fourth electrical signal; and calculating an impedance value between the output end and the receive end based on the third electrical signal and the fourth electrical signal, where correspondingly, the setting condition further includes: the impedance value is within a preset impedance range.

In an embodiment, the third electrical signal and the fourth electrical signal are direct-current signals.

In an embodiment, the preset condition is: an impedance value between the output end and the receive end that is calculated based on the first electrical signal and the second electrical signal is within a preset impedance range.

In an embodiment, the sports sensing apparatus includes an acceleration sensor and/or a gyroscope apparatus. The acceleration sensor is configured to detect sports characteristic data indicating an acceleration change, and the gyroscope apparatus is configured to detect sports characteristic data indicating an angle change.

In an embodiment, after the intelligent device sets the sports mode to the swimming mode, the processor 1140 is configured to: read a software instruction in the memory, and further execute the software instruction to implement the following operations:

driving the output end to output a fifth electrical signal and driving the receive end to receive a sixth electrical signal; and setting the sports mode to a non-swimming mode if a frequency of the sixth electrical signal does not match a frequency of the fifth electrical signal.

In an optional implementation, after the intelligent device sets the sports mode to the swimming mode, the processor 1140 is configured to: read a software instruction in the memory, and further execute the software instruction to implement the following operations:

driving the sports sensing apparatus to detect second sports characteristic data; and setting the sports mode to the non-swimming mode if the second sports characteristic data does not match the preset sports characteristic data.

An embodiment of this application further provides a computer-readable storage medium. The computer-readable storage medium stores an instruction. When the instruction is run on a computer, the computer is enabled to perform one or more operations in any one of the foregoing methods. When the components of the device for setting a sports mode are implemented in a form of a software functional unit and sold or used as an independent product, the components may be stored in the computer-readable storage medium.

Based on such an understanding, an embodiment of this application further provides a computer program product including an instruction. The technical solutions of this application essentially, or the part contributing to the conventional technology, or all or some of the technical solutions may be implemented in a form of a software product. The computer software product is stored in a storage medium and includes several instructions for instructing a computer device (which may be a personal computer, a server, a device, or the like) or a processor included to perform all or some of the operations of the methods described in the embodiments of this application.

The "first" in names such as "first electrical signal" mentioned in the embodiments of this application is used only for name identification, and does not represent the first in order. This rule is also applicable to "second" and the like.

It may be learned from the foregoing descriptions of the implementations that a person skilled in the art may clearly understand that all or some of the operations of the methods in the embodiments may be implemented by using software and a universal hardware platform. Based on such an understanding, the technical solutions of this application may be implemented in a form of a software product. The computer software product may be stored in a storage medium, such as a read-only memory (ROM)/RAM, a magnetic disk, an optical disc, or the like, and includes several instructions for instructing a computer device (which may be a personal computer, a server, or a network communications device such as a router) to perform the methods described in the embodiments or some parts of the embodiments of this application.

The embodiments in this specification are all described in a progressive manner. For same or similar parts in the embodiments, reference may be made to these embodiments, and each embodiment focuses on a difference from other embodiments. Especially, method and device embodiments are basically similar to a system embodiment, and therefore are described briefly. For related parts, refer to partial descriptions in the system embodiment. The described device and system embodiments are merely examples. The modules described as separate parts may or may not be physically separate, and parts displayed as modules may or may not be physical modules, that is, may be located at one position, or may be distributed on a plurality of network units. Some or all of the modules may be selected based on actual requirements to achieve the objectives of the solutions of the embodiments. A person of ordinary skill in the art may understand and implement the embodiments of this application without creative efforts.

The foregoing descriptions are merely example implementations of this application, but are not intended to limit the protection scope of this application.

What is claimed is:

1. A method for setting a sports mode of an intelligent device, comprising:
    outputting a first electrical signal via an output end;
    receiving a second electrical signal via a receive end, wherein the output end and the receive end are two metal endpoints on an outer surface of the intelligent device;
    obtaining first sports characteristic data detected by a sports sensing apparatus mounted in the intelligent device; and
    setting the sports mode to a swimming mode when a setting condition of the swimming mode is met, wherein the setting condition is met when a variation between the second electrical signal and the first electrical signal meets a preset condition, and the first sports characteristic data matches preset sports characteristic data corresponding to the swimming mode.

2. The method of claim 1, wherein the preset condition is met when a frequency of the second electrical signal matches a frequency of the first electrical signal.

3. The method of claim 2, wherein the first electrical signal and the second electrical signal are square wave signals.

4. The method of claim 2, further comprising:
    outputting a third electrical signal via the output end;
    receiving a fourth electrical signal via the receive end;
    calculating an impedance value between the output end and the receive end based on the third electrical signal and the fourth electrical signal, wherein the setting condition is met when the impedance value is within a preset impedance range.

5. The method of claim 4, wherein the third electrical signal and the fourth electrical signal are direct-current (DC) signals.

6. The method of claim 1, wherein the preset condition is met when an impedance value between the output end and the receive end that is calculated based on the first electrical signal and the second electrical signal is within a preset impedance range.

7. The method of claim 1, wherein the sports sensing apparatus comprises an acceleration sensor and a gyroscope apparatus, the acceleration sensor is configured to detect sports characteristic data indicating an acceleration change, and the gyroscope apparatus is configured to detect sports characteristic data indicating an angle change.

8. The method of claim 1, further comprising:
    outputting a fifth electrical signal via the output end;
    receiving a sixth electrical signal via the receive end; and
    setting the sports mode to a non-swimming mode when a frequency of the sixth electrical signal does not match a frequency of the fifth electrical signal.

9. The method of claim 1, further comprising:
    obtaining second sports characteristic data detected by the sports sensing apparatus; and
    setting the sports mode to a non-swimming mode when the second sports characteristic data does not match the preset sports characteristic data.

10. A computer program product for setting a sports mode of an intelligent device, the computer program product being embodied in a non-transitory computer readable medium and comprising computer instructions, which when executed by a processor, cause the intelligent device to perform operations, the operations comprising:
    outputting a first electrical signal via an output end;
    receiving a second electrical signal via a receive end, wherein the output end and the receive end are two metal endpoints on an outer surface of the intelligent device;
    obtaining first sports characteristic data detected by a sports sensing apparatus mounted in the intelligent device; and
    setting the sports mode to a swimming mode when a setting condition of the swimming mode is met, wherein the setting condition is met when a variation between the second electrical signal and the first electrical signal meets a preset condition, and the first sports characteristic data matches preset sports characteristic data corresponding to the swimming mode.

11. The computer program product of claim 10, wherein the operations further comprise:
    outputting a third electrical signal via the output end;
    receiving a fourth electrical signal via the receive end;
    calculating an impedance value between the output end and the receive end based on the third electrical signal and the fourth electrical signal, wherein the setting condition is met when the impedance value is within a preset impedance range.

12. The computer program product of claim 10, wherein the operations further comprise:
    outputting a fifth electrical signal via the output end;
    receiving a sixth electrical signal via the receive end; and
    setting the sports mode to a non-swimming mode when a frequency of the sixth electrical signal does not match a frequency of the fifth electrical signal.

13. The computer program product of claim 10, wherein the operations further comprise:
    obtaining second sports characteristic data detected by the sports sensing apparatus; and
    setting the sports mode to a non-swimming mode when the second sports characteristic data does not match the preset sports characteristic data.

14. An intelligent device, comprising:
    a sports sensing apparatus;
    a non-transitory memory comprising instructions; and
    a processor coupled to the non-transitory memory, wherein the instructions, when executed by the processor, cause the intelligent device to:
    output a first electrical signal via an output end;
    receive a second electrical signal via a receive end, wherein the output end and the receive end are two metal endpoints on an outer surface of the intelligent device;
    obtain first sports characteristic data detected by the sports sensing apparatus; and
    set a sports mode to a swimming mode when a setting condition of the swimming mode is met, wherein the setting condition is met when a variation between the second electrical signal and the first electrical signal meets a preset condition, and the first sports characteristic data matches preset sports characteristic data corresponding to the swimming mode.

15. The intelligent device of claim 14, wherein the preset condition is met when a frequency of the second electrical signal matches a frequency of the first electrical signal.

16. The intelligent device of claim 15, wherein the first electrical signal and the second electrical signal are square wave signals.

17. The intelligent device of claim 15, wherein the computer-executable instructions further cause the intelligent device to:
output a third electrical signal via the output end;
receive a fourth electrical signal via the receive end;
calculate an impedance value between the output end and the receive end based on the third electrical signal and the fourth electrical signal, wherein the setting condition is met when the impedance value is within a preset impedance range.

18. The intelligent device of claim 17, wherein the third electrical signal and the fourth electrical signal are direct-current (DC) signals.

19. The intelligent device of claim 14, wherein the sports sensing apparatus comprises an acceleration sensor and a gyroscope apparatus, the acceleration sensor is configured to detect sports characteristic data indicating an acceleration change, and the gyroscope apparatus is configured to detect sports characteristic data indicating an angle change.

20. The intelligent device of claim 14, wherein the computer-executable instructions further cause the intelligent device to:
obtain second sports characteristic data detected by the sports sensing apparatus; and
set the sports mode to a non-swimming mode when the second sports characteristic data does not match the preset sports characteristic data.

* * * * *